US011014986B2

(12) United States Patent
Reichert et al.

(10) Patent No.: US 11,014,986 B2
(45) Date of Patent: May 25, 2021

(54) CRYSTALS OF ANTI-HUMAN PD-1 MONOCLONAL ANTIBODIES

(71) Applicants: Paul Reichert, Montville, NJ (US); Winifred W. Prosise, Ramsey, NJ (US); Giovanna Scapin, New York, NY (US); Xiaoyu Yang, Basking Ridge, NJ (US); Ramesh Kashi, Warren, NJ (US); Corey Strickland, Martinsville, NJ (US); Merck Sharp & Dohme Corp., Rahway, NJ (US)

(72) Inventors: Paul Reichert, Montville, NJ (US); Winifred W. Prosise, Ramsey, NJ (US); Giovanna Scapin, New York, NY (US); Xiaoyu Yang, Basking Ridge, NJ (US); Ramesh Kashi, Warren, NJ (US); Corey Strickland, Martinsville, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/553,254

(22) PCT Filed: Feb. 22, 2016

(86) PCT No.: PCT/US2016/018843
§ 371 (c)(1),
(2) Date: Aug. 24, 2017

(87) PCT Pub. No.: WO2016/137850
PCT Pub. Date: Sep. 1, 2016

(65) Prior Publication Data
US 2018/0237524 A1    Aug. 23, 2018

Related U.S. Application Data

(60) Provisional application No. 62/121,867, filed on Feb. 27, 2015.

(51) Int. Cl.
C07K 16/28    (2006.01)
C07K 16/00    (2006.01)

(52) U.S. Cl.
CPC .......... *C07K 16/2818* (2013.01); *C07K 16/00* (2013.01); *C07K 2317/24* (2013.01); *C07K 2317/76* (2013.01)

(58) Field of Classification Search
CPC ..... G01N 23/20; G01N 29/58; C07K 16/2818
See application file for complete search history.

(56) References Cited

U.S. PATENT DOCUMENTS

| | | | |
|---|---|---|---|
| 6,875,432 B2 | 4/2005 | Liu et al. | |
| 7,615,213 B2 | 11/2009 | Kasaian et al. | |
| 7,666,413 B2 | 2/2010 | Liu et al. | |
| 7,833,525 B2 | 11/2010 | Shenoy et al. | |
| 7,998,477 B2 | 8/2011 | Yakovlevsky et al. | |
| 8,034,906 B2 | 10/2011 | Borhani et al. | |
| 8,142,776 B2 | 3/2012 | Liu et al. | |
| 8,168,760 B2 | 5/2012 | Borhani et al. | |
| 8,703,126 B2 | 8/2014 | Liu et al. | |
| 2013/0108651 A1 | 5/2013 | Carven et al. | |
| 2014/0234296 A1 | 8/2014 | Sharma et al. | |
| 2014/0314714 A1 | 10/2014 | Honjo et al. | |
| 2014/0348841 A1 | 11/2014 | Schebye et al. | |

FOREIGN PATENT DOCUMENTS

| | | |
|---|---|---|
| AU | 2010200784 A1 | 3/2010 |
| CA | 2918888 | 1/2015 |
| EP | 1324776 B1 | 4/2001 |
| EP | 1201123 A2 | 6/2007 |
| EP | 1801123 A3 | 11/2007 |
| EP | 2238985 B1 | 8/2012 |
| JP | 2005502589 A | 1/2005 |
| JP | 2010507670 A | 3/2010 |
| JP | 2014515017 A | 6/2014 |
| WO | 2002072636 A2 | 9/2002 |
| WO | 2006133486 A1 | 12/2006 |
| WO | 2008057240 A2 | 5/2008 |
| WO | 2012135035 | 10/2012 |
| WO | 2012135408 | 10/2012 |
| WO | 2014004436 | 1/2014 |
| WO | 2015011199 | 1/2015 |

(Continued)

OTHER PUBLICATIONS

Ahamed et al. "Phase Behaviour of Intact Monoclonal Antibody", Biochemical Journal, Jul. 2007, vol. 93, pp. 610-619.*
Zang et al., "Towards Protein Crystallization as a Process Step in Downstream Processing of Therapeutic Antibodies: Screening and Optimization at Microbatch Scale", PLoS ONE, Sep. 2011, 6(9):1-8.*
McPherson, A. Current Approaches to Macromolecular Crystallization. European Journal of Biochemistry. 1990. vol. 189, pp. 1-23.*

(Continued)

*Primary Examiner* — Suzanne M Noakes
(74) *Attorney, Agent, or Firm* — Sarah L. Hooson; Catherine D. Fitch

(57) ABSTRACT

Crystals of pembrolizumab and structurally similar anti-PD-1 monoclonal antibodies are provided, as well as methods of producing such crystals, and uses of compositions comprising such antibody crystals, e.g. in treatment of cancers. The present invention satisfies these needs and more by providing pembrolizumab crystals and a method producing pembrolizumab crystals. One embodiment of the method of the invention produces crystals suitable for X-ray diffraction, and the inventors herein used such crystals to solve the three-dimensional structure of pembrolizumab to 2.3 Å resolution.

18 Claims, 14 Drawing Sheets
(1 of 14 Drawing Sheet(s) Filed in Color)
Specification includes a Sequence Listing.

(56) References Cited

FOREIGN PATENT DOCUMENTS

| WO | 2016024228 | 2/2016 |
|---|---|---|
| WO | 2016168716 A1 | 10/2016 |

OTHER PUBLICATIONS

Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Moon et al., "A synergistic approach to protein crystallization: Combination of a fixed-arm carrier with surface entropy reduction", Protein Science, 2010, 19:901-913.*
Weber, P.C. Overview of Crystallization Methods. Methods in Enzymology. 1997. vol. 276, pp. 13-22.*
Harris et al., Comparison of the conformations of two intact monoclonal antibodies with hinges, Immunological Reviews, 1998, pp. 35-43, vol. 163.
Harris et al., Crystallization of Intact Monoclonal Antibodies, Proteins: Structure, Function, and Genetics, 1995, pp. 285-289, vol. 23, No. 2.
Harris et al., Crystallographic Structure of an Intact IgG1 Monoclonal Antibody, Journal of Molecular Biochemistry, 1998, pp. 861-872, vol. 275.
Harris et al., Refined Structure of an Intact IgG2a Monoclonal Antibody, Biochemistry—American Chemical Society, 1997, pp. 1581-1597, vol. 36.
Ollmann Saphire et al., Crystal Structure of a Neutralizing Human IgG Against HIV-1: A Template for Vaccine Design, Science, 2001, pp. 1155-1159, vol. 293.
Ollmann Saphire et al., Crystallization and preliminary structure determination of an intact human immunoglobulin, b12: an antibody that broadly neutralizes primary isolates of HIV-1, Acta Crystallographica Section D: Biological Crystallography, 2001, pp. 168-171, D57.
Scapin et al., Structure of full-length human anti-PD1 therapeutic IgG4 antibody pembrolizumab, Nature Structural & Molecular Biology, 2015, pp. 953-958, vol. 22, No. 12.
Sharma et al., Preparation, purification and crystallization of antibody Fabs and single-chain Fv domains, Immunology Methods Manual: The Comprehensive Sourcebook of Techniques, 1997, pp. 15-37, vol. 1.
Baker, M., Upping the ante on antibodies, Nature Biotechnology, 2005, pp. 1065-1072, vol. 23.
Basu, et al., Protein crystals for the delivery of biopharmaceuticals, Expert Opinion on Biological Therapy, 2004, pp. 301-317, vol. 4(3).
Davies, et al., Structural Determinants of Unique Properties of Human IgG4-Fc, Journal of Molecular Biology, 2014, pp. 630-644, vol. 426(3).
Emsley, et al., Features and development of Coot, Biological Crystallography, 2010, pp. 486-501, D66.
Giege, et al., Crystallogenesis of Biological Macromolecules: Facts and Perspectives, Acta Crystallogr., 1994, pp. 339-350, D50.
McCoy, et al., Phaser crystallographic software, Journal of Applied Crystallography, 2007, pp. 658-674, vol. 40.
McPherson, et al., Current approaches to macromolecular crystallization, Eur. J. Biochem., 1990, pp. 1-23, vol. 189.
Murshudov, et al., Refinement of Macromolecular Structures by the Maximum-Likelihood Method, Acta Cryst., 1997, pp. 240-255, D53.
Reichert, et al., Monoclonal antibody successes in the clinic, Nature Biotechnology, 2005, pp. 1073-1078, vol. 23.
Vonrhein, et al., Data processing and analysis with the autoPROC toolbox, Acta Crystallographica Section D, Biological Crystallography, 2011, pp. 293-302, D67.
WHO Drug Information, vol. 27, No. 2, pp. 161-162 (2013).
Yang, M. et al., Crystalline monoclonal antibodies for subcutaneous delivery, Proceedings of the National Academy of Sciences USA, 2003, 6934-6939, 100-12.
Hamid et al., Safety and Tumor Responses with Lambrolizumab (Anti-PD-1) in Melanoma, New Eng. J. Med., 2013, 134-144, 369(2).
Trilisky, Egor, Crystallization and Liquid-Liquid Phase Separation of Monoclonal Antibodies and Fc-Fusion Proteins: Screening Results, Biotechnology Progress, 2011, 1054-1067, vol. 27, No. 4.
Zhou, Shuxia et al., Biotherapeutic Formulation Factors Affecting Metal Leachables from Stainless Steel Studied by Design of Experiments, AAPS PharmSciTech, 2012, 284-294, 13(1).
Bernstein, J., Bioavailability, Polymorphism of molecular crystals, 2007, 324-330 (translated pp. 1-9), Ch. 7.3.2.
Bernstein, J., Bioavailability, Polymorphism of molecular crystals, 2007, 324-330, Ch. 7.3.2.
McDermott, et al., PD-1 as a potential target in cancer therapy, Cancer Medicine, 2013, pp. 662-673, WO.
Morissette, Sherry L. et al., High-throughput crystallization: polymorphs, salts, co-crystals and solvates of pharmaceutical solids, Advanced Drug Delivery Reviews, 2004, 275-300, 56.

* cited by examiner

Light chain CDR1 (SEQ ID NO:1)
Arg Ala Ser Lys Gly Val Ser Thr Ser Gly Tyr Ser Tyr Leu His Light chain CDR2 (SEQ ID NO:2)
Leu Ala Ser Tyr Leu Glu Ser Light chain CDR3 (SEQ ID NO:3)
Gln His Ser Arg Asp Leu Pro Leu Thr

FIG.1

Heavy chain CDR1 (SEQ ID NO:4)

Asn Tyr Tyr Met Tyr

Heavy chain CDR2 (SEQ ID NO:5)

Gly Ile Asn Pro Ser Asn Gly Gly Thr Asn Phe Asn Glu Lys Phe Lys Asn

Heavy chain CDR3 (SEQ ID NO:6)

Arg Asp Tyr Arg Phe Asp Met Gly Phe Asp Tyr

FIG.2

Heavy chain (SEQ ID NO:7)

```
QVQLVQSGVE VKKPGASVKV SCKASGYTFT NYYMYWVRQA PGQGLEWMGG  50
INPSNGGTNF NEKFKNRVTL TTDSSTTTAY MELKSLQFDD TAVYYCARRD 100
YRFDMGFDYW GQGTTVTVSS ASTKGPSVFP LAPCSRSTSE STAALGCLVK 150
DYFPEPVTVS WNSGALTSGV HTFPAVLQSS GLYSLSSVVT VPSSSLGTKT 200
YTCNVDHKPS NTKVDKRVES KYGPPCPPCP APEFLGGPSV FLFPPKPKDT 250
LMISRTPEVT CVVVDVSQED PEVQFNWYVD GVEVHNAKTK PREEQFNSTY 300
RVVSVLTVLH QDWLNGKEYK CKVSNKGLPS SIEKTISKAK GQPREPQVYT 350
LPPSQEEMTK NQVSLTCLVK GFYPSDIAVE WESNGQPENN YKTTPPVLDS 400
DGSFFLYSRL TVDKSRWQEG NVFSCSVMHE ALHNHYTQKS LSLSLGK    447
```

FIG.3A

Light chain (SEQ ID NO:8)

EIVLTQSPAT LSLSPGERAT LSCRASKGVS TSGYSYLHWY QQKPGQAPRL 50

LIYLASYLES GVPARFSGSG SGTDFTLTIS SLEPEDFAVY YCQHSRDLPL 100

TFGGGTKVEI KRTVAAPSVF IFPPSDEQLK SGTASVVCLL NNFYPREAKV 150

QWKVDNALQS GNSQESVTEQ DSKDSTYSLS STLTLSKADY EKHKVYACEV 200

THQGLSSPVT KSFNRGEC 219

FIG.3B

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial
<220> FEATURE:
<223> OTHER INFORMATION: Antibody Light Chain CDR

<400> SEQUENCE: 1

Arg Ala Ser Lys Gly Val Ser Thr Ser Gly Tyr Ser Tyr Leu His
1               5                   10                  15

<210> SEQ ID NO 2
<211> LENGTH: 7
<212> TYPE: PRT
<213> ORGANISM: Artificial
<220> FEATURE:
<223> OTHER INFORMATION: Antibody Light Chain CDR

<400> SEQUENCE: 2

Leu Ala Ser Tyr Leu Glu Ser
1               5

<210> SEQ ID NO 3
<211> LENGTH: 9
<212> TYPE: PRT
<213> ORGANISM: Artificial
<220> FEATURE:
<223> OTHER INFORMATION: Antibody Light Chain CDR

<400> SEQUENCE: 3

Gln His Ser Arg Asp Leu Pro Leu Thr
1               5

<210> SEQ ID NO 4
<211> LENGTH: 5
<212> TYPE: PRT
<213> ORGANISM: Artificial
<220> FEATURE:
<223> OTHER INFORMATION: Antibody Heavy Chain CDR

<400> SEQUENCE: 4

Asn Tyr Tyr Met Tyr
1               5

<210> SEQ ID NO 5
<211> LENGTH: 17
<212> TYPE: PRT
```

```
<213> ORGANISM: Artificial
<220> FEATURE:
<223> OTHER INFORMATION: Antibody Heavy Chain CDR

<400> SEQUENCE: 5
```

Gly Ile Asn Pro Ser Asn Gly Gly Thr Asn Phe Asn Glu Lys Phe Lys
1               5                   10                  15

Asn

```
<210> SEQ ID NO 6
<211> LENGTH: 11
<212> TYPE: PRT
<213> ORGANISM: Artificial
<220> FEATURE:
<223> OTHER INFORMATION: Antibody Heavy Chain CDR

<400> SEQUENCE: 6
```

Arg Asp Tyr Arg Phe Asp Met Gly Phe Asp Tyr
1               5                   10

```
<210> SEQ ID NO 7
<211> LENGTH: 447
<212> TYPE: PRT
<213> ORGANISM: Artificial Sequence
<220> FEATURE:
<223> OTHER INFORMATION: HUMANIZED ANTIBODY HEAVY CHAIN

<400> SEQUENCE: 7
```

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

```
Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 8
<211> LENGTH: 218
<212> TYPE: PRT
<213> ORGANISM: Artificial Sequence
<220> FEATURE:
<223> OTHER INFORMATION: HUMANIZED LIGHT CHAIN

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

-continued

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

CRYSTALS OF ANTI-HUMAN PD-1 MONOCLONAL ANTIBODIES

CROSS-REFERENCE TO RELATED APPLICATIONS

This application is a § 371 National Stage Application of PCT/US2016/018843, international filing date of Feb. 22, 2016, which claims the benefit of U.S. Provisional Application Ser. No. 62/121,867, filed Feb. 27, 2015.

FIELD OF THE INVENTION

The present invention relates generally to crystalline forms of monoclonal antibodies. More specifically, the invention relates to crystals of pembrolizumab and structural variants thereof, pharmaceutical compositions comprising such antibody crystals, and the use of such compositions in the treatment of cancer.

BACKGROUND OF THE INVENTION

Many tumors produce antigens that lead to an endogenous immune response against the tumor. However, this response is often ineffective because tumor cells can activate key immune-checkpoints that cause localized immune suppression. One of these immune checkpoints is the human cell surface receptor PD-1 (programmed death-1 or programmed cell death-1), which is an inhibitory signaling receptor expressed on the surface of activated T cells. Activation of PD-1 inhibitory signaling by the binding of one of its ligands, PD-L1 or PD-L2, results in the inhibition of T-cell-mediated immune responses against tumor cells. To counter this PD-1 pathway-mediated inhibition of the anti-tumor immune response against tumors, several companies are developing monoclonal antibodies (mAbs) that bind to human PD-1 and block the interaction between PD-1 and its ligands.

One of these anti-PD-1 mAbs is pembrolizumab, a humanized IgG4 mAb that is approved in the United States for the treatment of patients with unresectable or metastatic melanoma and disease progression following ipilimumab and, if BRAF V600 mutation positive, a BRAF inhibitor. The efficacy and safety of pembrolizumab in the treatment of a number of other cancer indications is being investigated.

Pembrolizumab is currently formulated for intravenous (IV) infusion, and lyophilized and solution formulations of pembrolizumab comprising 25 mg/ml of the mAb are described in WO2012/135408. However, a high concentration formulation designed to be administered subcutaneously would be a desirable alternative, in part because it could enable patients to self-administer pembrolizumab.

Therapeutic antibodies are traditionally prepared in lyophilized form or in solution. Lyophilized forms may exhibit enhanced long-term stability, but require reconstitution prior to use, making them less than ideal for self-administration. Solution formulations do not require reconstitution, but may suffer from reduced stability and typically require cold storage prior to use. Both lyophilized and solution formulations may fail to provide sufficiently high concentrations to allow for high dose delivery by subcutaneous administration, because 1.2 ml is the maximum preferred volume for subcutaneous administration (Yang, M. X. et al., *Proc. Nat'l. Acad. Sci.* (*USA*) 100:6934-1939 (2003)). However, high concentration solution formulations of antibodies, if achievable, may also be prone to dropping out of solution, or may be too viscous to be delivered in a narrow gauge needle, e.g. as required for subcutaneous administration, particularly self-administration.

One proposed approach for achieving high concentration antibody formulations is to prepare the formulation with antibody crystals, see, e.g., Yang et al., supra; U.S. Pat. No. 7,833,525 and WO2012/135035. The rationales for preparing therapeutic antibody compositions of antibody crystals include improved stability of protein crystals in liquid solutions at room temperature, lower viscosity of high antibody concentration solutions and the ability to manipulate crystallization conditions to achieve different morphologies for desired controlled release properties (see, e.g., Yang et al., supra and Basu, S. K., et al., *Expert Opin. Biol. Thera.* 4:301-317 (2004)).

Antibodies are believed to be especially difficult to crystallize due to the flexibility of the heavy and light chains. While there have been numerous reports of crystallization of intact antibodies over the last 30 years, there have only been four structures deposited in the RCSB Protein databank, in contrast to over 800 structures deposited of Fab apo or complex structures. Researchers at Altus Pharmaceuticals were the first to describe crystallization methods to crystallize three commercially available monoclonal antibodies: rituximab, trastuzumab and infliximab (WO02/072636). Other published patent applications describe methods for the preparation of crystals of anti-IL-13 mAbs (WO2005/121177), anti-TNF alpha mAbs (WO2008/057240), anti-sclerostin mAbs (WO2012/135035) and anti-IL-23 mAbs (WO2014/004436). Despite these examples of methods for crystallizing antibodies, it is generally agreed in the art of protein crystallization that identifying suitable crystallization conditions for a particular antibody is still an empirical exercise, and that there is no general rule that can be applied to a particular antibody of interest to reliably predict what crystallization conditions will produce crystals of that antibody.

Thus, the need exists for methods to prepare crystalline forms of pembrolizumab. Such crystals may be useful for elucidating the structure of pembrolizumab by x-ray diffraction analysis and for preparing improved pharmaceutical compositions of pembrolizumab for the treatment of cancer.

SUMMARY OF THE INVENTION

The present invention satisfies these needs and more by providing pembrolizumab crystals and a method producing pembrolizumab crystals. One embodiment of the method of the invention produces crystals suitable for X-ray diffraction, and the inventors herein used such crystals to solve the three-dimensional structure of pembrolizumab to 2.3 Å resolution.

Thus, in one aspect, the invention provides a crystal of an anti-PD-1 antibody. The antibody is pembrolizumab, a pembrolizumab variant, or the antibody in a pembrolizumab biosimilar. In an embodiment, the crystal comprises the antibody and a solvent. In an embodiment, the length of the crystal is between any of the following ranges: 1 to 200 microns, 1 to 100 microns, 1 to 20 microns, 5 to 100 microns, 5 to 50 microns or 5 to 20 microns. In an embodiment, the antibody crystal is characterized by unit cell dimensions of a=63.5 to 78.9 Å, b=110.2 to 112.2 Å, c=262.5 to 306 Å, α=90, β=90, γ=90° and a space group of $P2_12_12_1$. In an embodiment, the antibody crystal can diffract X-rays to a resolution of 3.5 Å or better, i.e., at less than 3.5 Å.

In another aspect, the invention provides a method for producing crystals of an anti-PD-1 monoclonal antibody (mAb), wherein the mAb is pembrolizumab, a pembrolizumab variant, or the antibody in a pembrolizumab biosimilar. The method comprises: (a) exposing a solution of the mAb (antibody solution) to a precipitant solution at a temperature of at least 25° C. and no greater than 50° C. for a time sufficient for crystal formation (crystallization), and (b) harvesting the crystals. In an embodiment, the exposing step is performed at a temperature of no greater than about 40° C. to about 45° C. In one embodiment, the precipitant solution used in the method has a pH of about 4.0-5.0 and comprises 1.0 M to 2.5 M ammonium dihydrogen phosphate (ADP). In an embodiment, the precipitant solution also comprises a buffering agent in a sufficient amount to adjust the pH of the precipitant solution to pH 4.0 to 5.0. In an embodiment, the buffer is Tris-HCl or ammonium phosphate dibasic. In an embodiment, the antibody solution comprises the anti-PD-1 mAb at a concentration of 3 to 100 mg/ml, 10 to 90 mg/ml, 20 to 80 mg/ml, 30 to 70 mg/ml, 40 to 60 mg/ml or about 50 mg/ml. In an embodiment, the antibody is performed for at least any of 3, 4 or 5 days. In an embodiment, the antibody solution comprises 10 mM histidine, pH 5.6. In an embodiment, the antibody solution further comprises polysorbate at a maximum concentration of about 0.01%. In an embodiment, the exposing step comprises performing a crystallization technique selected from the group consisting of: hanging drop vapor diffusion, sitting drop vapor diffusion, dialysis, microbatch and batch. In an embodiment, the exposing step comprises mixing equal volumes of antibody solution and precipitant solution to form a crystallization mixture.

In another aspect, the invention provides a method for crystallizing an anti-PD-1 monoclonal antibody (mAb) from a solution comprising the anti-PD-1 mAb, wherein the antibody is pembrolizumab, a pembrolizumab variant, or the antibody in a pembrolizumab biosimilar. The method comprises: (a) combining the anti-PD-1 mAb solution with a precipitant solution and seed crystals of the anti-PD-1 mAb to produce a seeded crystallization mixture; (b) incubating the seeded crystallization mixture at a temperature of at least 20° C. and no greater than 40° C.; and (c) harvesting the crystals. In an embodiment, the incubating temperature is about 30° C. and the precipitant solution comprises a mixture selected from the group consisting of: (1) 20% polyethylene glycol 4000 (PEG 4K) and 20% isopropanol; (2) 18% polyethylene glycol 10000 (PEG 10K), 20% glycerol, 100 mM Tris-HCl, pH 8.5; and (3) 2.0 M ammonium dihydrogen phosphate and 100 mM Tris-HCl. In another embodiment, the incubating temperature is about 22° C. and the precipitant solution comprises a mixture selected from the group consisting of: (1) 25% PEG 4K, 100 mM Tris-HCl, pH 8.5 and 100 mM $CaCl_2$ and (2) 1.26 M ammonium sulfate, sodium acetate, pH 4.5 and 0.2 M NaCl. In some embodiments, the seed crystals are from a seed stock of crystals of the anti-PD-1 mAb that were produced by crystallization at a temperature of about 30° C. in a precipitant solution having a pH of 4.0 to 5.0 and comprising 1.0 to 2.5 M ADP.

In yet another aspect, the invention provides a pharmaceutical composition comprising (a) crystals of an anti-PD-1 antibody, wherein the antibody is pembrolizumab, a pembrolizumab variant, or the antibody in a pembrolizumab biosimilar and (b) at least one pharmaceutically acceptable excipient. In an embodiment, the excipient performs at least one function selected from encapsulating the crystals, embedding the crystals and stably maintaining the crystals.

In some embodiments, the average length of the crystals in the composition is 1 to 20 microns, 5 to 20 microns, 5 to 50 microns or 5 to 100 microns. In an embodiment, the composition comprises the anti-PD-1 mAb crystals suspended in a liquid medium. In an embodiment, the anti-PD-1 mAb concentration in the composition is at least about 50 mg/ml and no greater than about 250 mg/ml. In another embodiment, the composition is a solid that has been prepared by dehydrating or lyophilizing a liquid suspension of the crystals. In an embodiment, at least 95%, 97% or 99% of the biological activity of the anti-PD-1 mAb is present after storage of the liquid or solid pharmaceutical composition for at least one month at room temperature (e.g. 20° C.-25° C.).

In another aspect, the invention provides a container which comprises any of the above pharmaceutical compositions. The container may be a single dose vial, multidose vial, pre-filled syringe or self-injection device. In an embodiment, the container comprises a single dose of about 200 to about 250 mg of the anti-PD-1 mAb, i.e., pembrolizumab, a pembrolizumab variant, or a pembrolizumab biosimilar.

In a still further aspect, the invention comprises a method of treating a human subject for a cancer, which comprises administering to the patient a therapeutically effective amount of any of the above pharmaceutical compositions. In an embodiment, the cancer is a solid tumor, e.g., bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC), or triple negative breast cancer. In another embodiment, the cancer is a Heme malignancy, e.g., acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL). In an embodiment, the pharmaceutical composition comprises at least 200 mg/ml of pembrolizumab and is administered subcutaneously. In an embodiment, a tissue section of the cancer removed from the subject prior to a first administration of the pharmaceutical composition tested positive for expression of one or both of PD-L1 and PD-L2. In an embodiment, at least 50% of the tumor cells in the tissue section tested positive for PD-L1 expression by an immunohistochemical (IHC) assay.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows amino acid sequences of the light chain CDR sequences for pembrolizumab and for pembrolizumab variants described herein (SEQ ID NO:1-3).

FIG. 2 shows amino acid sequences of the heavy chain CDR sequences for pembrolizumab and for pembrolizumab variants described herein (SEQ ID NO:4-6).

FIGS. 3A and 3B show amino acid sequences of the heavy chain (FIG. 3A) and light chain (FIG. 3B) for pembrolizumab (SEQ ID NOs: 7 and 8, respectively).

DETAILED DESCRIPTION

I. Abbreviations

Figure 4A:
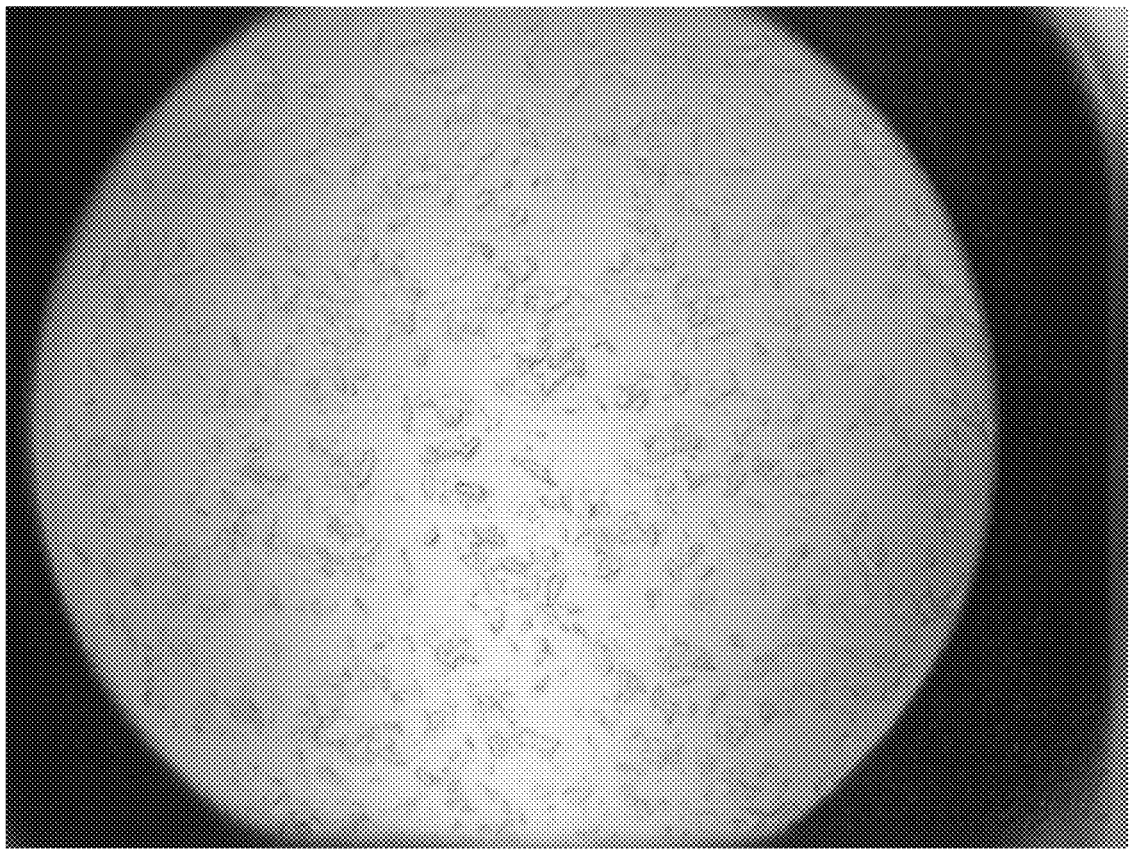
FIGS. 4A and 4B show photomicrographs of crystals within a pembrolizumab crystalline suspension, obtained by vapor diffusion at 30° C. using a precipitant solution of 2.0 M ammonium dihydrogen phosphate, 100 mM Tris-HCl. The photomicrographs, at 100× magnification, were taken after 3 days using a SONICC imaging system, with FIG. 4A produced using the SHG mode and FIG. 4B produced using the UV-TPEF mode. See Example 1.

Throughout the detailed description and examples of the invention the following abbreviations will be used:

ADP Ammonium dihydrogen phosphate
AHP Ammonium hydrogen phosphate
CDR Complementarity determining region
CHO Chinese hamster ovary
DFS Disease free survival
FR Framework region
IHC Immunohistochemistry or immunohistochemical
NCBI National Center for Biotechnology Information
NCI National Cancer Institute
PD Progressive disease
PD-1 Programmed Death 1
PD-L1 Programmed Cell Death 1 Ligand 1
PD-L2 Programmed Cell Death 1 Ligand 2
PFS Progression free survival
PR Partial response
OR Overall response
OS Overall survival
Q2W One dose every two weeks
Q3W One dose every three weeks
QD One dose per day
RECIST Response Evaluation Criteria in Solid Tumors
SD Stable disease
VH Immunoglobulin heavy chain variable region
VK Immunoglobulin kappa light chain variable region

II. Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"About" when used to modify a numerically defined parameter (e.g., the concentration of a component in a solution) means that the parameter may vary by as much as 10% above or below the stated numerical value for that parameter. For example, a composition comprising about 200 mg/ml of a specified antibody may have between 180 mg/ml and 220 mg/ml of the antibody. Similarly, a temperature of about 30° C. means any temperature between 27° C. and 33° C.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also include in vitro and ex vivo treatments, e.g., of a cell, by a reagent, diagnostic, binding composition, or by another cell. The term "subject" includes any organism, preferably an animal, more preferably a mammal (e.g., rat, mouse, dog, cat, rabbit) and most preferably a human.

As used herein the term "antibody" refers to a tetramer that includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain defines a constant region primarily responsible for effector function. The variable regions of each light/heavy chain pair form the antibody binding site. Thus, in general, an intact antibody has two binding sites. Except in bifunctional or bispecific antibodies, the two binding sites are usually identical.

Typically, the variable regions of each of the heavy and light chains comprise three hypervariable regions, also called complementarity determining regions (CDRs), which are located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4 (i.e. CDRL1, CDRL2 and CDRL3 in the light chain variable domain and CDRH1, CDRH2 and CDRH3 in the heavy chain variable domain). The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

Ammonium dihydrogen phosphate (NH$_4$H$_2$PO4) or ADP as used herein is synonymous with ammonium phosphate monobasic, mono-ammonium phosphate and prim-ammonium phosphate.

Ammonium hydrogen phosphate ((NH$_4$)$_2$HPO$_4$) or AHP as used herein is synonymous with ammonium phosphate dibasic, diammonium hydrogen phosphate and diammonium hydrogen phosphate.

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Particularly preferred cancers that may be treated in accordance with the present invention include those characterized by elevated expression of one or both of PD-L1 and PD-L2 in tested tissue samples.

"Concentration", when used with reference to a crystalline antibody suspension of the present invention, refers to the amount of antibody (e.g., pembrolizumab) present in a given macroscopic unit volume of solution. The term concentration is used in its customary sense despite the inherent heterogeneity of the suspension, as compared to a traditional solution. The concentration of antibody in a crystalline suspension is equal to the concentration of an equivalent sample in which the antibody is not in crystalline form.

"Conservatively modified variants" or "conservative substitution" refers to substitutions of amino acids are known to those of skill in this art and may be made generally without altering the biological activity of the resulting molecule, even in essential regions of the polypeptide. Such exemplary substitutions are preferably made in accordance with those set forth in Table 1 as follows:

TABLE 1

Exemplary Conservative Amino Acid Substitutions

| Original residue | Conservative substitution |
|---|---|
| Ala (A) | Gly; Ser |
| Arg (R) | Lys, His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

"Consists essentially of," and variations such as "consist essentially of" or "consisting essentially of," as used throughout the specification and claims, indicate the inclusion of any recited elements or group of elements, and the optional inclusion of other elements, of similar or different nature than the recited elements, that do not materially change the basic or novel properties of the specified dosage regimen, method, or composition. As a non-limiting example, a pharmaceutical composition that consists essentially of antibody crystals and a specific pharmaceutically acceptable excipient may also include one or more other excipients that do not materially affect the properties of the pharmaceutical composition.

"Anti-PD-1 mAb crystal" or "crystalline anti-PD-1 mAb" as used herein refers to a crystal containing the antibody arranged in a lattice structure that repeats periodically in three dimensions. In contrast, a solid, amorphous form of the mAb, e.g., such as produced by lyophilizing a mAb dissolved in a solution, does not display the optical properties such as refractive index and birefringence that are typical of a crystalline antibody form.

As used herein, and with regard to crystallization methods based on dialysis, "dialysis solution" refers to the solution against which a solution of pembrolizumab (the "antibody solution") is dialyzed to drive formation of the crystalline antibody of the present invention. "Retentate" refers to the antibody solution after dialysis, which may include crystals of the antibody, which are harvested. The antibody solution/retentate are on one side of the dialysis membrane, and the dialysis solution is on the opposite side.

The terms "micron" and "micrometer" are used interchangeably herein and each means 1/1000000th of a meter.

"Monoclonal antibody" or "mAb" or "Mab", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

"PD-L1" or "PD-L2" expression as used herein means any detectable level of expression of the designated PD-L protein on the cell surface or of the designated PD-L mRNA within a cell or tissue. PD-L protein expression may be detected with a diagnostic PD-L antibody in an IHC assay of a tumor tissue section or by flow cytometry. Alternatively, PD-L protein expression by tumor cells may be detected by PET imaging, using a binding agent (e.g., antibody fragment, affibody and the like) that specifically binds to the desired PD-L target, e.g., PD-L1 or PD-L2. Techniques for detecting and measuring PD-L mRNA expression include RT-PCR and real-time quantitative RT-PCR.

Several approaches have been described for quantifying PD-L1 protein expression in IHC assays of tumor tissue sections. See, e.g., Thompson, R. H., et al., PNAS 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012).

One approach employs a simple binary end-point of positive or negative for PD-L1 expression, with a positive result defined in terms of the percentage of tumor cells that exhibit histologic evidence of cell-surface membrane staining. A tumor tissue section is counted as positive for PD-L1 expression is at least 1%, and preferably 5% of total tumor cells.

In another approach, PD-L1 expression in the tumor tissue section is quantified in the tumor cells as well as in infiltrating immune cells, which predominantly comprise lymphocytes. The percentage of tumor cells and infiltrating immune cells that exhibit membrane staining are separately quantified as <5%, 5 to 9%, and then in 10% increments up to 100%. For tumor cells, PD-L1 expression is counted as negative if the score is <5% score and positive if the score is ≥5%. PD-L1 expression in the immune infiltrate is reported as a semi-quantitative measurement called the adjusted inflammation score (AIS), which is determined by multiplying the percent of membrane staining cells by the intensity of the infiltrate, which is graded as none (0), mild (score of 1, rare lymphocytes), moderate (score of 2, focal infiltration of tumor by lymphohistiocytic aggregates), or severe (score of 3, diffuse infiltration). A tumor tissue section is counted as positive for PD-L1 expression by immune infiltrates if the AIS is ≥5.

The level of PD-L mRNA expression may be compared to the mRNA expression levels of one or more reference genes that are frequently used in quantitative RT-PCR, such as ubiquitin C.

In some embodiments, a level of PD-L1 expression (protein and/or mRNA) by malignant cells and/or by infiltrating immune cells within a tumor is determined to be "overexpressed" or "elevated" based on comparison with the level of PD-L1 expression (protein and/or mRNA) by an appropriate control. For example, a control PD-L1 protein or mRNA expression level may be the level quantified in nonmalignant cells of the same type or in a section from a matched normal tissue. In some preferred embodiments, PD-L1 expression in a tumor sample is determined to be elevated if PD-L1 protein (and/or PD-L1 mRNA) in the sample is at least 10%, 20%, or 30% greater than in the control.

As used herein, "pembrolizumab" means (a) the IgG4 monoclonal antibody with the structure described in *WHO Drug Information*, Vol. 27, No. 2, pages 161-162 (2013) and which is manufactured by, or on behalf of, Merck Sharp & Dohme Corp. (MSD), a company that controls or is controlled by MSD, or a successor in interest thereof (individual and collectively, "MSD"). Each light chain of pembrolizumab comprises the three CDR sequences shown in FIG. 1 (SEQ ID NO:1 as CDRL1, SEQ ID NO:2 as CDRL2 and SEQ ID NO:3 as CDRL3) and each heavy chain of pembrolizumab comprises the CDR sequences shown in FIG. 2 (SEQ ID NO:4 as CDRH1, SEQ ID NO:5 as CDRH2 and SEQ ID NO:6 as CDRH3). The full length heavy and light chains of pembrolizumab comprise the heavy and light chain sequences shown in FIG. 3 (SEQ ID NO:7 and SEQ ID NO:8, respectively).

A pembrolizumab biosimilar means a biological product manufactured by an entity other than MSD and which is approved by a regulatory agency in any country for marketing as a pembrolizumab biosimilar. In an embodiment, a pembrolizumab biosimilar comprises a pembrolizumab variant as the drug substance. In an embodiment, a pembrolizumab biosimilar has the same amino acid sequence as pembrolizumab.

As used herein, a "pembrolizumab variant" means a monoclonal antibody which comprises heavy chain and light chain sequences that are identical to those in pembrolizumab (SEQ ID NO:7 and 8, respectively), except for having three, two or one conservative amino acid substitutions at positions that are located outside of the light chain CDRs and six, five, four, three, two or one conservative amino acid substitutions that are located outside of the heavy chain CDRs, e.g., the variant positions are located in the framework regions or the constant region. In other words, pembrolizumab and a pembrolizumab variant comprise identical CDR sequences, but differ from each other due to having a conservative amino acid substitution at no more than three or six other positions in their full length light and heavy chain sequences, respectively. A pembrolizumab variant is substantially the same as pembrolizumab with respect to the following properties: binding affinity to PD-1 and ability to block the binding of each of PD-L1 and PD-L2 to PD-1.

A "precipitant" is a compound that decreases the solubility of a polypeptide, such as an antibody, in a concentrated solution. In batch crystallization methods, the precipitant is included in the "precipitant solution," and in bulk dialysis methods the precipitant is included in the "dialysis solution." Precipitants induce crystallization by forming an energetically unfavorable precipitant-depleted layer around the polypeptide molecules. To minimize the relative amount of this depletion layer, the polypeptides form associations and, ultimately, crystals. This process is explained in Weber (1991) *Advances in Protein Chemistry* 41:1. Various precipitants are known in the art and include: ammonium sulfate, ethanol, isopropanol, 1,2 propanediol, 3-ethyl-2,4 pentanediol; and many of the polyglycols, such as polyethylene glycol (e.g. PEG 300 and PEG 400). In addition to precipitants, other materials are sometimes added to the polypeptide precipitant solution. These include buffers, such as Tris or HEPES, to adjust the pH of the solution (and hence surface charge on the peptide) and salts, such as sodium chloride, lithium chloride and sodium citrate, to reduce the solubility of the polypeptide.

As used herein, the term "therapeutically effective amount" or "effective amount" refers to an amount of an anti-PD-1 antibody that when administered alone or in combination with an additional therapeutic agent to a cell, tissue, or subject is effective to treat a cancer. When applied to the anti-PD-1 antibody administered alone, a therapeutically effective amount refers to that ingredient alone. When applied to a combination, a therapeutically effective amount refers to combined amounts of the anti-PD-1 antibody and the additional therapeutic agent that result in the therapeutic effect, whether administered in combination, serially or simultaneously.

"Tissue Section" refers to a single part or piece of a tissue sample, e.g., a thin slice of tissue cut from a sample of a normal tissue or of a tumor.

"Treat" or "treating" a cancer as used herein means to administer a pharmaceutical composition of the invention to a subject having a cancer, or diagnosed with a cancer, to achieve at least one positive therapeutic effect, such as for example, reduced number of cancer cells, reduced tumor size, reduced rate of cancer cell infiltration into peripheral organs, or reduced rate of tumor metastasis or tumor growth. Positive therapeutic effects in cancer can be measured in a number of ways (See, W. A. Weber, *J. Nucl. Med.* 50:15-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a combination of the invention is any of PR, CR, OR, PFS, DFS and OS. PFS, also referred to as "Time to Tumor Progression" indicates the length of time during and after treatment that the cancer does not grow, and includes the amount of time patients have experienced a CR or PR, as well as the amount of time patients have experienced SD. DFS refers to the length of time during and after treatment that the patient remains free of disease. OS refers to a prolongation in life expectancy as compared to naive or untreated individuals or patients. In some preferred embodiments, response to a combination of the invention is any of PR, CR, PFS, DFS, OR or OS that is assessed using RECIST 1.1 response criteria. The treatment regimen for a combination of the invention that is effective to treat a cancer patient may vary according to factors such as the disease state, age, and weight of the patient, and the ability of the therapy to elicit an anti-cancer response in the subject. While an embodiment of any of the aspects of the invention may not be effective in achieving a positive therapeutic effect in every subject, it should do so in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

"Tris" (2-Amino-2-hydroxymethyl-propane-1,3-diol) as used herein is synonymous with TRIS, Tris base, Trizma, Trisamine, THAM, Tromethamine, Trometamol, Trometh-ane, and Trisaminol.

"Tumor" as it applies to a subject diagnosed with, or suspected of having, a cancer refers to a malignant or potentially malignant neoplasm or tissue mass of any size, and includes primary tumors and secondary neoplasms. A solid tumor is an abnormal growth or mass of tissue that usually does not contain cysts or liquid areas. Different types of solid tumors are named for the type of cells that form them. Examples of solid tumors are sarcomas, carcinomas, and lymphomas. Leukemias (cancers of the blood) generally do not form solid tumors (National Cancer Institute, Dictionary of Cancer Terms).

"Tumor burden" also referred to as "tumor load", refers to the total amount of tumor material distributed throughout the body. Tumor burden refers to the total number of cancer cells or the total size of tumor(s), throughout the body, including lymph nodes and bone narrow. Tumor burden can be determined by a variety of methods known in the art, such as, e.g. by measuring the dimensions of tumor(s) upon removal from the subject, e.g., using calipers, or while in the body using imaging techniques, e.g., ultrasound, bone scan, computed tomography (CT) or magnetic resonance imaging (MRI) scans.

The term "tumor size" refers to the total size of the tumor which can be measured as the length and width of a tumor. Tumor size may be determined by a variety of methods known in the art, such as, e.g. by measuring the dimensions of tumor(s) upon removal from the subject, e.g., using calipers, or while in the body using imaging techniques, e.g., bone scan, ultrasound, CT or MRI scans.

III. Antibody Crystallization

The present invention is based, in part, on the identification of crystallization conditions for pembrolizumab. The crystallization conditions comprise a unique combination of: (1) a precipitant solution which comprises a high salt concentration (i.e., ADP at 1.0 M to 2.5 M or 1.5 M to 2.0 M) and has an acidic pH (i.e., pH of any of the following 4.0 to 5.0, 4.2 to 4.8, 4.4 to 4.6 or 4.5); and (2) a high temperature (i.e., at least 25° C. and up to 50° C.). In an embodiment, the pH may be maintained within the required range by including a buffering agent in the precipitant solution. Suitable buffering agents include, e.g., Tris-HCl, ammonium hydrogen phosphate, histidine and ammonium hydroxide. The pH of the precipitant solution is preferably determined for the temperature at which the crystallization is to be performed, which in one embodiment is a temperature of 27° C. to about 30° C. The crystallization conditions of the invention are compatible with several crystallization techniques and are capable of producing crystalline forms of the anti-PD-1 mAb in a variety of lengths, including 1 to 20 microns and 5 to 100 microns, as well as crystals with low resolution (e.g., 3.5 Å) or high resolution (e.g., 2.3 Å), depending on the intended use of the crystals. weaker than 3.5 a diffraction resolution, including of varying diffraction characteristics.

Various methods of protein crystallization are known. Giege et al. (1994) *Acta Crystallogr.* D50:339; McPherson (1990) *Eur. J. Biochem.* 189:1. Such techniques include hanging drop vapor diffusion (McPherson (1976) *J. Biol. Chem.* 251:6300), sitting drop vapor diffusion, microbatch and dialysis.

Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water vaporizes from the drop and transfers to the reservoir, the precipitant concentration increases to a level optimal for crystallization. Since the system is in equilibrium, these optimum conditions are maintained until the crystallization is complete. The hanging drop method differs from the sitting drop method in the vertical orientation of the protein solution drop within the system.

In the microbatch method, polypeptide is mixed with precipitants to achieve supersaturation, and the vessel is sealed and set aside until crystals appear.

In the dialysis method, polypeptide is retained on one side of a dialysis membrane which is placed into contact with a solution containing precipitant. Equilibration across the membrane increases the precipitant concentration thereby causing the polypeptide to reach supersaturation levels.

Some of these techniques were used to prepare pembrolizumab crystals of the invention, as described in greater detail in Examples 1-7. The high-throughput examples are best suited for screening to optimize the precipitant solution, rather than for large scale crystal production.

The anti-PD-1 mAb solution used in a crystallization method of the invention will have an antibody concentration of 3 to 100 mg/ml and is conveniently provided in a buffer of about 10 mM histidine, at a pH of about 5.5.

With regard to large scale production of anti-PD-1 mAb crystals, e.g. for therapeutic use, Examples 5 and 9-11 summarize batch crystallization protocols. In an embodiment, a batch method for crystallizing pembrolizumab from a solution comprises preparing a crystallization mixture which comprises at least 10 mg/ml pembrolizumab in 1.8 to 2.5 M ADP and has a pH of about 4.4 to 4.6. In an embodiment, the crystallization mixture further comprises an additive selected from the group consisting of 3% 1,5 di-amino pentane di-hydrochloride; 3% isopropanol and 4% propylene glycol. Crystals may be harvested from a batch crystallization mixture using methods known in the art, such as centrifugation, dialysis, and various filtration methods, including hollow fiber tangential flow filtration.

The anti-PD-1 mAb crystals may be analyzed by various methods to examine or characterize their physical properties, such as crystal size, shape, surface morphology, total surface area and porosity. Such analytical techniques include, e.g., electron diffraction and sold state nuclear magnetic resonance (ssNMR), light microscopy, transmission electron microscopy, scanning electron microscopy, atomic force microscopy, and various light scattering techniques.

The biological activity and/or biophysical properties of the anti-PD-1 mAb in crystals of the invention may be analyzed by "re-dissolving" or solubilizing the antibody crystal in a buffer suitable for the desired analytical technique. For example, the solubilized anti-PD-1 mAb may be analyzed by one or more of ELISA, size exclusion chromatography, SDS PAGE, and dynamic light scattering. The inventors herein contemplate that the crystallization conditions described herein will be useful in batch crystallization techniques to prepare crystalline suspensions of pembrolizumab and of structurally similar anti-PD-1 mAbs, i.e., pembrolizumab variants and pembrolizumab biosimilars. Due to the high crystallization temperature used (at least 25° C. and up to 50° C.), the inventors contemplate that crystalline suspensions produced using these conditions, and pharmaceutical compositions comprising such crystals, may be stored at room temperature for periods of at least one month with little to no change in biological activity or stability of the anti-PD-1 mAb.

Anti-PD-1 mAb (pembrolizumab, a pembrolizumab variant or pembrolizumab biosimilar) that has been solubilized from antibody crystals prepared in accordance with the present invention should retain the properties of the pre-crystallization starting material within acceptable tolerances. Acceptable tolerances for the various functional parameters may vary based on the intended use, but with regard to binding affinity or biological activity, may include retention of at least 80%, at least 90% or at least 95% of the original (non-crystallized) affinity or activity. For example, the ability of the anti-PD-1 mAb to block binding of PD-L1 to PD-1 may be measured using the method described in Example 12.

As described in Examples 11-12 herein, the biological activity and biophysical properties of pembrolizumab obtained from dissolving pembrolizumab crystals and pembrolizumab that had not been crystallized were compared using ELISA and size exclusion chromatography and were determined to be substantially similar. These results support the use of pharmaceutical compositions comprising pembrolizumab crystals for the therapeutic treatment of human subjects.

IV. Pharmaceutical Compositions

To prepare pharmaceutical compositions, the anti-PD-1 mAb crystals of the present invention, or anti-PD-1 mAb solubilized from such crystals, are mixed with at least one pharmaceutically acceptable excipient. See, e.g., *Remington's Pharmaceutical Sciences* and *U.S. Pharmacopeia: National Formulary*, Mack Publishing Company, Easton, Pa. (1984). It is not required that the anti-PD-1 mAb crystals used in a pharmaceutical composition of the invention have any particular diffraction quality, as long as the biological activity and stability of the antibody are maintained within the desired range.

In some embodiments, the excipient(s) is added directly to the crystallization liquor during or after crystallization. In other embodiments, the crystals are first harvested from the liquor, washed by suspension in a stabilizing solution, harvested from the stabilizing solution and then suspended in a liquid solution which comprises the excipient(s). The composition of the liquid may be any pharmaceutically acceptable medium, and may include, e.g., aqueous solutions and water in oil mixtures.

Pharmaceutical compositions of crystals in a solid form may be prepared by drying a liquid suspension comprising the crystals and the desired excipient(s), e.g., by passing a stream of nitrogen, air or inert gas over the crystals, by air drying, vacuum drying or lyophilization. The moisture content in the final product will typically be less than 10%, 7%, 5% or 3% by weight.

A pharmaceutical composition comprising pembrolizumab that has been solubilized from pembrolizumab crystals in a liquid suspension or in a dried solid may be prepared by adding a desired quantity of the crystals to a pharmaceutically acceptable dissolution buffer and incubating at 4° C. until the crystals have dissolved. In an embodiment, the dissolution buffer comprises 10 mM histidine, pH 5.6, 0.02% polysorbate 80 and up to 4% sucrose w/v. In an embodiment, any particulates in the resulting composition are removed prior to administration, e.g., by centrifugation or filtration.

V. Treatment Methods

Determination of the appropriate dose of a pharmaceutical composition of the invention for treating a particular cancer in a particular patient may be made by the clinician, e.g., using parameters or factors known or suspected in the art to affect treatment or predicted to affect treatment. For example, the physician may choose to initiate treatment with a dose that is somewhat less than the optimum dose or the approved dose and then increase the dose by small increments until the desired or optimum effect is achieved relative to any negative side effects.

In an embodiment, the dose and administration route of the composition will provide a median exposure to the pembrolizumab antibody that is substantially similar to that provided by un-crystallized pembrolizumab at a dose of 200 mg Q2W or Q3W.

These and other aspects of the invention, including the exemplary specific embodiments listed below, will be apparent to the skilled artisan from the teachings contained herein combined with common knowledge in the art.

VI. Exemplary Specific Embodiments of the Invention

1. A crystal of an anti-PD-1 monoclonal antibody (mAb), wherein the mAb is pembrolizumab, a pembrolizumab variant, or the antibody in a pembrolizumab biosimilar.

2. The crystal of embodiment 1, wherein the crystal is characterized by having a length in a range selected from the group consisting of: 1 to 200 microns, 1 to 100 microns, 1 to 20 microns, 5 to 100 microns, 5 to 50 microns 5 to 40 microns, 5 to 30 microns, 5 to 20 microns, 5 to 10 microns, 10 to 100 microns, 10 to 50 microns and 10 to 20 microns.

3. The crystal of embodiment 3, wherein the crystal is characterized by having a length of 5 to 10 microns, 5 to 20 microns or 5 to 40 microns.

4. The crystal of embodiment 2, wherein the crystal is characterized by having a length of 50 to 100 microns.

5. The crystal of any of embodiments 1 to 4, which is characterized by unit cell dimensions of a=63.5 to 78.9 Å, b=110.2 to 112.2 Å, c=262.5 to 306 Å, α=90, β=90, γ=90° and a space group of $P2_12_12_3$.

6. The crystal of any of the above embodiments, which is capable of diffracting X-rays to a resolution selected from the group consisting of 2.3 Å to 3.5 Å, 2.3 Å to 3.0 Å, 2.3 Å to 2.75 Å, 2.3 Å to 2.5 Å and 2.3 Å.

7. The crystal of any of the above embodiments, which is suspended in a liquid medium comprising additional crystals of the same anti-PD-1 mAb.

8. The crystal of any of the above embodiments, wherein the anti-PD-1 mAb is pembrolizumab.

9. A method for producing crystals of an anti-PD-1 monoclonal antibody (mAb), wherein the mAb is pembrolizumab, a pembrolizumab variant, or the antibody in a pembrolizumab biosimilar and the method comprises exposing a solution comprising the anti-PD-1 mAb to a precipitant solution at a temperature that is at least 25° C. and is no greater than 50° C., 45° C., 40° C. or 37° C. for a time sufficient for crystal formation, wherein the precipitant solution has a pH of 4.0 to 5.0 and comprises 1.0 M to 2.5 M ammonium dihydrogen phosphate.

10. The method of embodiment 9, wherein the exposing step comprises mixing the antibody solution and the precipitant solution to form a crystallization mixture and applying a crystallization process to the mixture.

11. The method of embodiment 10, wherein the crystallization process is selected from the group consisting of hanging drop vapor diffusion, sitting drop vapor diffusion and batch.

12. The method of embodiment 11, wherein the crystallization process is a batch process and the method further comprises seeding the crystallization mixture with crystals of the anti-PD-1 mAb.

13. The method of any of embodiments 9 to 12, wherein the antibody concentration in the crystallization mixture is about 10 mg/ml or about 20 mg/ml.

14. The method of embodiment 9, wherein the exposing step comprises dialyzing the antibody solution against the precipitant solution using a 30 kD molecular weight cut-off membrane.

15. The method of any of embodiments 9 to 14, wherein the antibody solution comprises the anti-PD-1 mAb at a concentration of 2 to 200 mg/ml, 3 to 100 mg/ml, 10 to 90 mg/ml, 20 to 80 mg/ml, 30 to 70 mg/ml, 40 to 60 mg/ml or about 50 mg/ml.

16. The method of any of embodiments 9 to 15, wherein the precipitant solution has a pH selected from the group consisting of 4.2 to 4.8, 4.4 to 4.6 and 4.5.

17. The method of any of embodiments 9 to 16, wherein the precipitant solution further comprises a buffering agent.

18. The method of embodiment 17, wherein the buffering agent is Tris-HCl, ammonium hydrogen phosphate, ammonium hydroxide or histidine.

19. The method of any of embodiments 9 to 18, wherein the precipitant solution consists essentially of 1.5 M to 2.0 M ammonium dihydrogen phosphate and 100 to 120 mM Tris-HCl.

20. The method of any of embodiments 9 to 17, wherein the precipitant solution comprises a mixture of ammonium dihydrogen phosphate and ammonium hydrogen phosphate.

21. The method of embodiment 20, wherein the precipitant solution consists essentially of 1.9 M ammonium dihydrogen phosphate and 0.09 M ammonium hydrogen phosphate.

22. The method of any of embodiments 9 to 21, wherein the exposing step is performed for at least 3, 4 or 5 days at a temperature of about 30° C.

23. A method for crystallizing an anti-PD-1 monoclonal antibody (mAb) from a solution comprising the anti-PD-1 mAb, wherein the antibody is pembrolizumab, a pembrolizumab variant, or the antibody in a pembrolizumab biosimilar and the method comprises: (a) combining the anti-PD-1 mAb solution with a precipitant solution and seed crystals of the anti-PD-1 mAb to produce a seeded crystallization mixture; (b) incubating the seeded crystallization mixture at a temperature of at least 20° C. and no greater than 40° C.; and (c) harvesting the crystals.

24. The method of embodiment 23, wherein the incubating temperature is about 30° C. and the precipitant solution comprises a mixture selected from the group consisting of: (1) 20% polyethylene glycol 4000 (PEG 4K) and 20% isopropanol; (2) 18% polyethylene glycol 10000 (PEG 10K), 20% glycerol, 100 mM Tris-HCl, pH 8.5; and (3) 2.0 M ammonium dihydrogen phosphate and 100 mM Tris-HCl.

25. The method embodiment 23, wherein the incubating temperature is about 22° C. and the precipitant solution comprises a mixture selected from the group consisting of: (1) 25% PEG 4K, 100 mM Tris-HCl, pH 8.5 and 100 mM $CaCl_2$ and (2) 1.26 M ammonium sulfate, sodium acetate, pH 4.5 and 0.2 M NaCl.

26. The method of any of embodiments 23 to 25, wherein the seed crystals are from a seed stock of crystals of the anti-PD-1 mAb that were produced by a method of any of embodiments 9 to 22.

27. The method of any of embodiments 9 to 26, wherein the anti-PD-1 mAb is pembrolizumab.

28. An anti-PD-1 mAb crystal produced by a method as defined in any of embodiments 9 to 27.

29. A pharmaceutical composition comprising (a) crystals of an anti-PD-1 monoclonal antibody (mAb), wherein the antibody is pembrolizumab, a pembrolizumab variant, or the antibody in a pembrolizumab biosimilar and (b) at least one pharmaceutically acceptable excipient.

30. The composition of embodiment 29, wherein the excipient performs at least one function selected from the group consisting of encapsulating the crystals, embedding the crystals and stably maintaining the crystals.

31. The composition of embodiment 29 or 30, wherein each of the anti-PD-1 mAb crystals is a crystal as defined in any of embodiments 1 to 8 or 27.

32. The composition of any of embodiments 29 to 31, which is a liquid.

33. The composition of any of embodiments 29 to 31, which is a solid.

34. The composition of any of embodiments 29 to 32, wherein the anti-PD-1 mAb concentration in the composition is at least 50 mg/ml, at least 100 mg/ml, at least 200 mg/ml or at least 250 mg/ml.

35. The composition of any of embodiments 29 to 34, wherein at least 95% of the biological activity of the anti-PD-1 mAb is present after storage of the composition for at least one month at 20° C. to 25° C.

36. A method of treating a human subject for a cancer, which comprises administering to the patient a therapeutically effective amount of a pharmaceutical composition of any of embodiments 29 to 35.

37. The method of embodiment 36, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CML), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

38. The method of embodiment 36 or 37, wherein the pharmaceutical composition comprises at least 200 mg/ml of the mAb and is administered subcutaneously.

39. The method of any of embodiments 36 to 38, wherein the cancer is a solid tumor and a tissue section of the cancer removed from the subject prior to a first administration of the pharmaceutical composition tested positive for expression of one or both of PD-L1 and PD-L2.

40. The method of embodiment 39, wherein at least 50% of the tumor cells in the tissue section tested positive for PD-L1 expression by an immunohistochemical (IHC) assay.

The broad scope of this invention is best understood with reference to the following examples, which are not intended to limit the inventions to the specific embodiments. The specific embodiments described herein are offered by way of example only, and the invention is to be limited by the terms of the appended claims, along with the full scope of equivalents to which such claims are entitled.

EXAMPLES

Example 1: Drop Vapor Diffusion Crystallization Screening of Pembrolizumab

A solution of 34 mg/ml of full-length pembrolizumab was prepared in 10 mM Histidine (pH 5.6). This solution was screened in sitting drop vapor diffusion experiments performed in MRC 96 well crystallization plates from Hampton Research (Aliso Viejo, Calif., USA) and four commercially available high throughput screens from Rigaku Corporation (Seattle, Wash., USA) and Jena Bioscience (Jena, Del., USA) Each screen consisted of 96 unique solutions, which are summarized in Table 2 below.

TABLE 2

Summary of Screen Solutions

| Manufacturer | Screen Name/Cat. No. | Solution Composition |
| --- | --- | --- |
| Rigaku Corp. | Wizard Classic 1 & 2/ EB-W12-B | 96 unique conditions primarily PEG, alcohol and high salt based |
| Rigaku Corp. | Wizard Cryo 1 & 2/ EB-C12-B | 96 unique conditions primarily PEG, alcohol and high salt based |
| Jena Biosciences | JB Screen Classic HTS1/ CS-201L | 96 unique conditions primarily PEG based |
| Jena Biosciences | JB Screen Classic HTS1/ CS-202L | 96 unique conditions primarily high salt based |

For each screen experiment, the pembrolizumab solution (0.2 ul) was mixed with a screen solution (0.2 ul) and layered over 80 ul of screen solution in a plate well using an Oryx crystallization robot from Douglas Instruments, Inc. (Hungerford, Berkshire, UK). Experiments were performed at each of 4° C., 18° C. and 30° C. for each screen solution; thus, a total of 1,152 different crystallization conditions were tested. The plate wells were monitored microscopically for crystal formation over time.

Figure 4B:
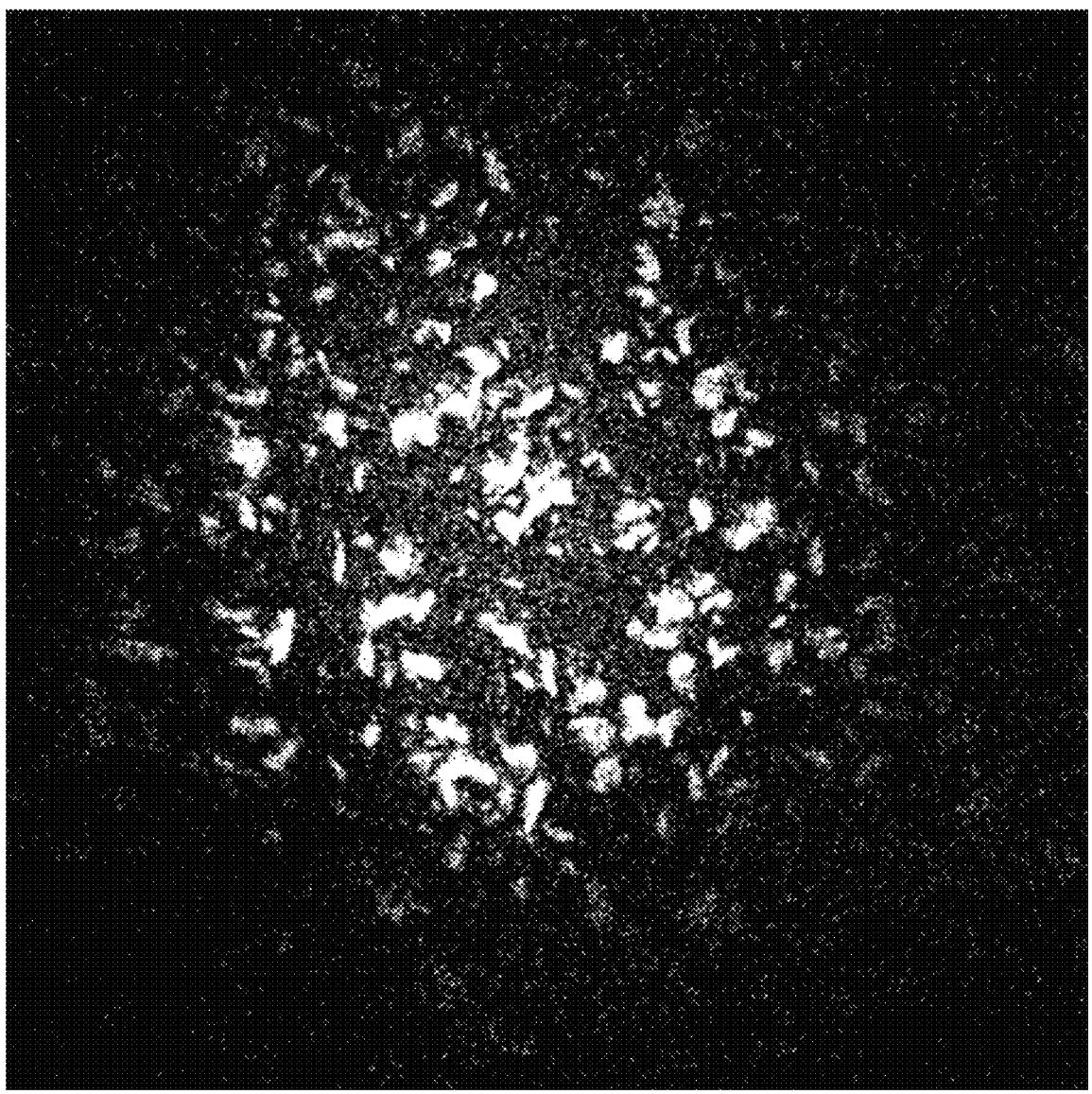

Crystals were observed after 3 days with only one of the tested conditions: 30° C. with the Jena 2 (Salt) #91 (100 mM Tris-HCl, pH 8.5, 2.0 M ammonium di-hydrogen phosphate). The crystals were visualized using a SONICC imaging system from Formulatrix (Bedford, Mass., USA). The SONICC system has two imaging methods, Second Harmonic Generation (SHG), which probes crystallinity, and Ultraviolet Two-Photon Excited Fluorescence (UV-TPEF), which is specific to proteinaceous samples. Images of the observed crystals are shown in FIG. 4A (SHG) and FIG. 4B (UV-TPEF).

Example 2: Free Interface Diffusion Crystallization Screening of Pembrolizumab

Based on crystals forming only at 30° C. in Example 1, this temperature was chosen to further investigate screening conditions for pembrolizumab using the free interface diffusion technique.

Figure 5A:
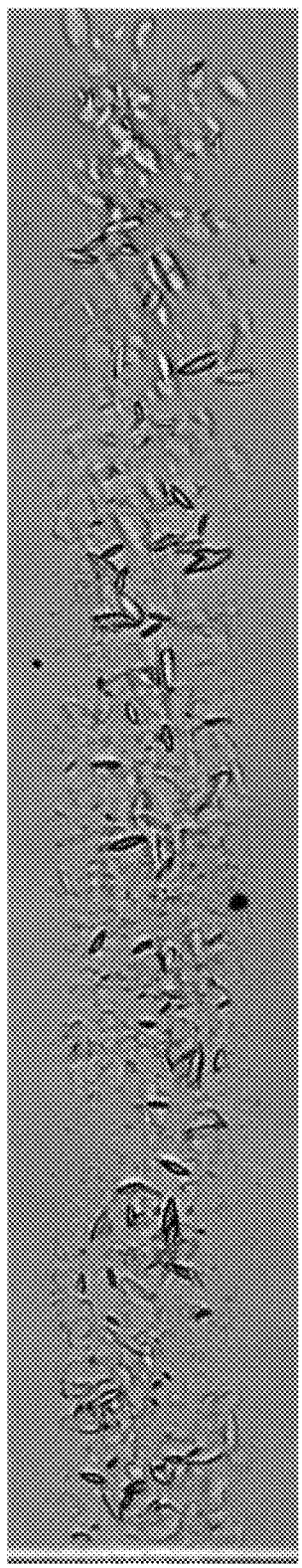
FIGS. 5A and 5B show photomicrographs of crystals within pembrolizumab crystalline suspensions, obtained by free interface diffusion at 30° C. using a precipitant solution of 2.0 M ammonium dihydrogen phosphate, 100 mM Tris in the presence (FIG. 5A) or absence (FIG. 5B) of 0.02% polysorbate 80. The photomicrographs, at 100× magnification, were taken after 2 days using a Fluidigm Automated Imaging system. See Example 2.
Figure 5B:
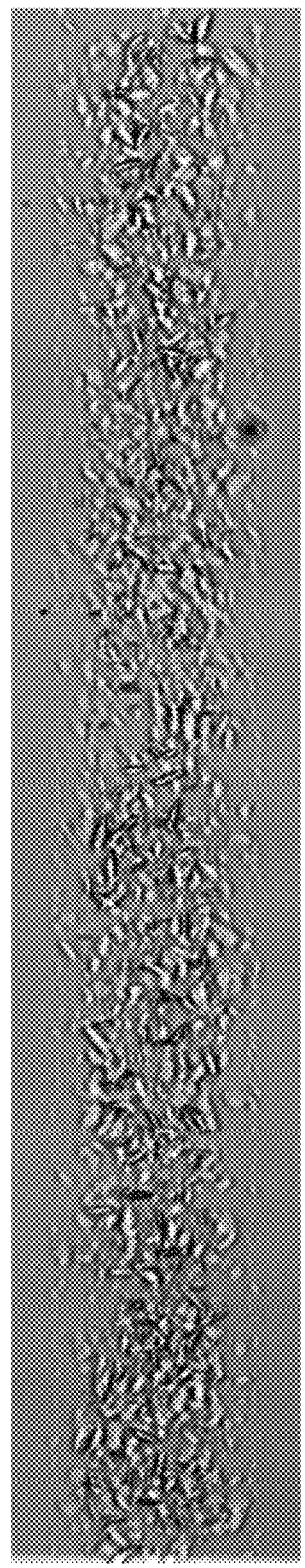

Antibody solutions with 34 mg/ml of pembrolizumab were prepared in 10 mM Histidine (pH 5.6) and with or without 0.02% polysorbate 80 and were screened with the same screen solutions used in Example 1 in Topaz chips and crystallizer from Fluidigm Corporation (South San Francisco, Calif., USA). The chips were incubated at 30° C. and monitored microscopically using a Fluidigm Automated Imaging system. Crystals were again observed only with the Jena 2 (Jena Bioscience) #91 solution: 100 mM Tris, pH 8.5, 2.0 M ammonium dihydrogen phosphate. Images of the observed crystals from the two different pembrolizumab solutions are shown in Figure FIG. 5A (antibody solution with 0.02% polysorbate 80) and FIG. 5B (antibody solution without polysorbate 80).

Example 3: Micro-Seeding Matrix Screening of Pembrolizumab

This example investigated conditions under which pembrolizumab could be crystallized from a solution seeded with pre-existing pembrolizumab crystals. The precipitant solutions screened were the same four commercially available screens described in Example 1.

A seed stock of pembrolizumab crystals was prepared from the crystal suspension produced in Example 1 (pembrolizumab crystals in 2.0 M ADP, 100 mM Tris-HCl) by combining 1 ul of the pembrolizumab crystal suspension and 99 ul of a stabilizing solution of 1.8 M ADP, 100 mM Tris-HCl (prepared by mixing appropriate amounts of stock solutions of 2.5 M ADP and 1M Tris-HCl, pH 8.5. An antibody solution of 34 mg/ml of pembrolizumab was prepared in 10 mM Histidine (pH 5.6). Sitting drop vapor diffusion experiments were performed in MRC 96 well crystallization plates (Hampton Research).

For each screen experiment, the pembrolizumab solution (0.3 ul) was mixed with a screen solution (0.3 ul) and 0.1 ul of the seed stock and layered over 80 ul of the screen solution in a plate well using the Oryx crystallization robot. Experiments were performed at each of 22° C. and 30° C. for each screen solution; thus, a total of 768 crystallization conditions were tested. The plate wells were monitored microscopically for crystals over time and crystals were observed microscopically after 1 week from the five conditions shown in Table 3 below. Visualization of the crystals by SONICC (UV positive) confirmed that the observed crystals were protein in content.

TABLE 3

Drop vapor diffusion conditions which produced pembrolizumab crystals after seeding.

| Temperature | Screen Solution |
| --- | --- |
| 30° C. | 20% PEG 4K, 20% isopropanol |
| 30° C. | 18% PEG 10K, 20% glycerol, 100 mM Tris, pH 8.5, 100 mM NaCl |
| 30° C. | 100 mM TRIS, pH 8.5, 2.M ammonium dihydrogen phosphate |
| 22° C. | 25% PEG 4K, 100 mM Tris, 100 mM CaCL$_2$ |
| 22° C. | 1.26M ammonium sulfate, acetate, pH 4.5/0.2M NaCl |

Example 4: Optimization of Vapor Diffusion Crystallization in ADP/Tris-HCl

Figure 6:
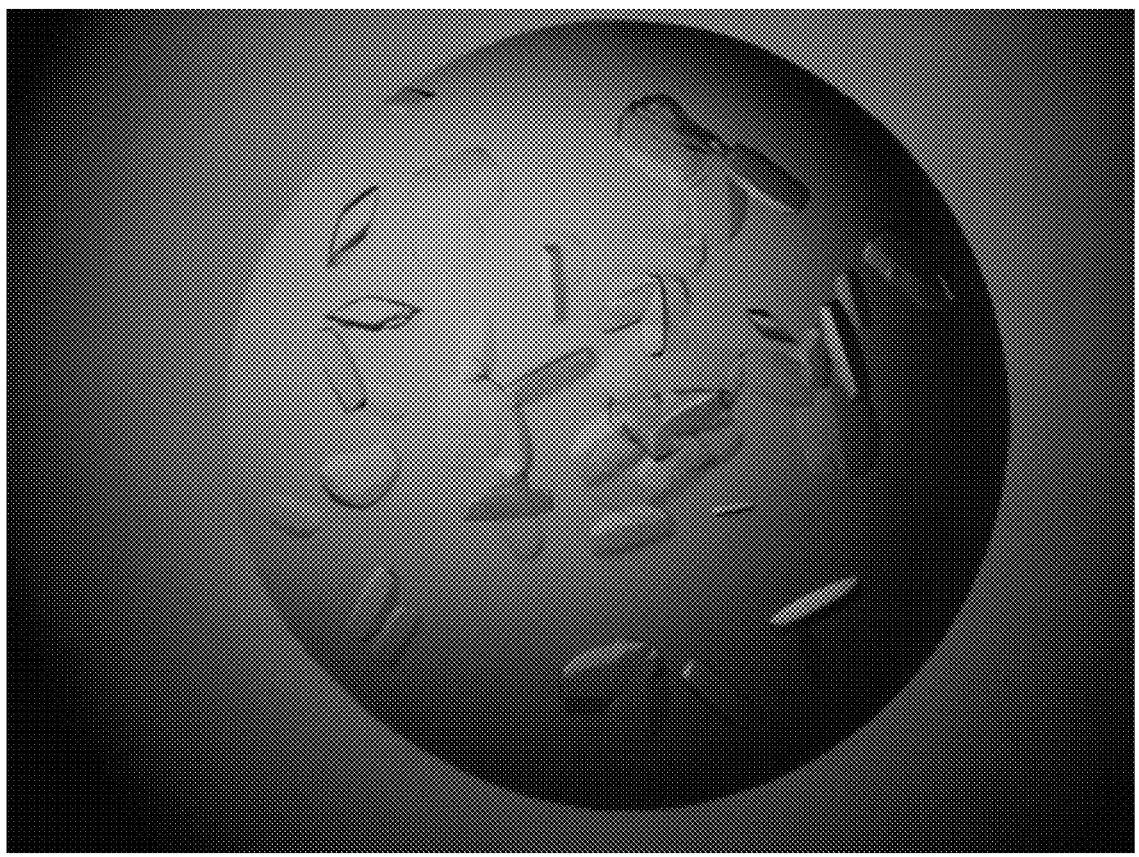
FIG. 6 shows photomicrographs of crystals within a pembrolizumab crystalline suspension, obtained by hanging drop vapor diffusion at 30° C. using a precipitant solution of 1.5 M ammonium dihydrogen phosphate, 100 mM Tris-HCl. The photomicrographs, at 100× magnification, were taken after 3 days using a Nikon SMZ1500 Stereo Microscope and Nikon ES400 camera imaging system. See Example 4.

To identify optimal ADP concentration and pH conditions suitable for preparing diffraction quality crystals, the following screening experiments were performed, which examined mixtures of 100 mM Tris-HCl at a pH varying between 8.8 to 9.4 and ADP at a concentration varying from 1.60 to 1.74 M. Pembrolizumab (34 mg/ml, 10 mM histidine, pH 5.6) was setup in hanging drop vapor diffusion experiments versus a custom optimization screen designed using the OptiMatrix Maker™ liquid handling system (Rigaku Corp., Seattle, Wash., USA) in a VDX 24 well (6×4 array) crystallization plate (Hampton Research). For each screen experiment, a hanging drop consisting of 1.0 ul protein+1.0 ul screen solution was placed on the underside of a 22 mm coverslip and placed on a well containing 1 ml of the screen solution such that the pH of the 100 mM Tris-HCl component was varied in the vertical 4 wells and the ADP concentration was varied in the horizontal over 6 wells. The plate was incubated at 30° C. and monitored microscopically over time. FIG. 6 shows a photomicrograph of crystals observed after 3 days in the 100 mM Tris-HCl, pH 8.0, 1.5 M ADP screen solution.

Example 5: Batch Crystallization of Pembrolizumab in ADP/Tris-HCl

Figure 7:
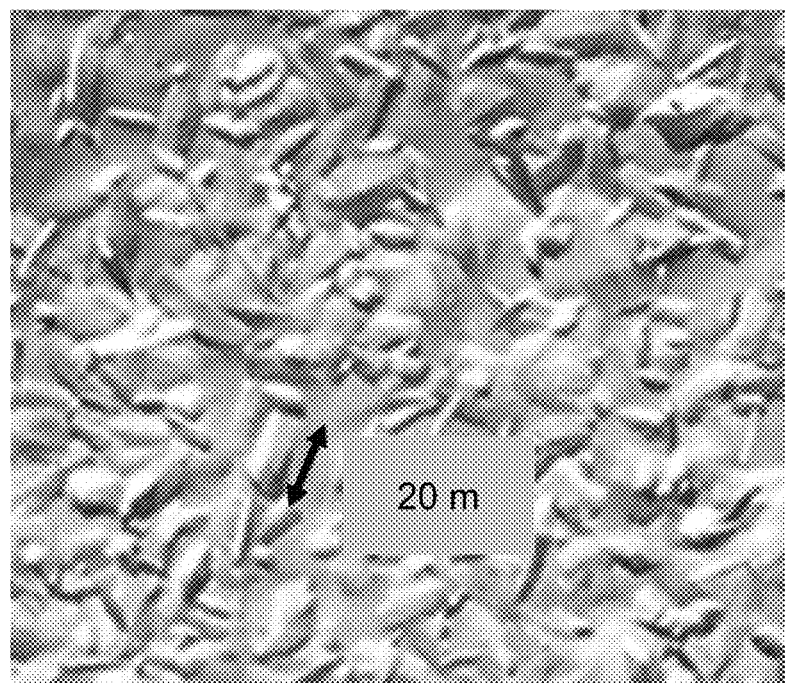
FIG. 7 shows a photomicrograph of crystals within a pembrolizumab crystalline suspension, obtained by batch crystallization at 30° C. using a precipitant solution of 1.8 M ammonium dihydrogen phosphate, 120 mM Tris-HCl. See Example 5. The photomicrograph, at 100× magnification, was taken after 5 days using a Nikon SMZ1500 Stereo Microscope and Nikon ES400 camera imaging system. The double-sided arrow indicates a crystal of about 20 micron in length.

A crystallization mixture was prepared by combining 10 ul of a 50 mg/ml pembrolizumab solution (10 mM histidine, pH 5.6) with 50 ul of 120 mM Tris-HCl, pH 8.5, 1.8 M ADP at 22° C. This crystallization mixture was placed in a Micro-Bridge (Hampton Research) placed inside the well of a VDX plate (Hampton Research). The well contained 1 ml of 100 mM Tris-HCl, pH 8.5, 1440 mM ADP. The well was sealed using a 22 mm glass coverslip and the plate incubated for 5 days at 30° C. A photomicrograph of the resulting crystalline suspension is shown in FIG. 7. Crystal sizes ranging from about 5 microns to at least about 20 microns were observed.

Example 6: Additive Screen to Optimize Vapor Diffusion Crystallization Conditions A solution of 34 mg/ml of pembrolizumab was prepared in 10 mM Histidine (pH 5.6). This pembrolizumab solution was screened in sitting drop vapor diffusion experiments against 96 precipitant solutions prepared using the Additive Screen HT™ kit (Hampton Research). This kit contains 96 different additive solutions.

For each additive, 80 ul of a precipitant solution containing 72 ul of 1.74 mM ADP, 100 mM Tris-HCl, pH 9.0 and 8.0 ul of an additive solution was added to the well of an MRC 96 well crystallization plate. The pembrolizumab solution (0.2 ul) was mixed with the well solution (0.2 ul) and layered over the 80 ul well solution using the Oryx crystallization robot (Douglas Instruments). The plate was sealed and incubated at 30° C. and monitored microscopically over time. Crystals were observed after 3-7 days. After 1 week, crystals were observed in the Tris, ADP precipitant solution that contained one of the following additives: (a) 3% 1,5 di-amino pentane di-hydrochloride, (b) 3% isopropanol or (c) 4% propylene glycol. However, crystals were not observed with any of the other 93 precipitant solutions, suggesting that the additives in those solutions retarded crystal nucleation or growth.

Example 7: X-ray Diffraction Analysis of Pembrolizumab Crystals

Diffraction quality crystals of full-length pembrolizumab were grown at 30° C. using a hanging drop technique. A 34 mg/ml solution of pembrolizumab in 10 mM Histidine, pH 5.6 (1 ul) was combined with 1.8 M ammonium dihydrogen phosphate, 100 mM Tris-HCl, pH 8.0 (1 ul). Crystals were harvested after 7 to 60 days and cryo-protected using a saturated (100%) sucrose solution in 1.5 M ammonium sulfate, 0.2 M NaCl or 35% ethylene glycol in 1.5 M ammonium sulfate, 0.2 M NaCl.

X-ray diffraction data were collected using synchrotron radiation at ID-17 (Argonne National Laboratory, Argonne, Ill., USA), and processed and scaled using autoPROC (Vonrhein C. et al., Acta Cryst. D67:293-302 (2011)). The best data set was obtained from the sucrose protected crystals, and extended to 2.28 angstroms (Å). Based on 24 data sets, crystals of pembrolizumab belong to the $P2_12_12_1$ system with a=63.5 to 78.9 Å, b=110.2 to 112.2 Å, c=262.5 to 306 Å and alpha=beta=gamma=90°.

The pembrolizumab structure was solved from the X-ray diffraction data using molecular replacement procedures as implemented in PHASER (McCoy A. J. et al., J. Appl. Cryst. 40:658-674 (2007)). The structure of a fab of an anti-IL- 23p19 mAb and an IgG4 FC structure (PDB entry 4C54, Davies A. M. et al., *J. Mol. Biol.*: 426(3):630-644 (2014)), with sugars and waters removed, were used as search models. Refinement was carried out initially with REFMAC (Murshudov G. N. et al., *Acta Crystall. D*53:240-25 (1997)) and subsequently with autoBUSTER (Bricogne G, et al. BUSTER 2.11.5. [Internet]. Cambridge 2011). Model building was done in COOT (Emsley P, et al., *Acta Cryst. D*66:486-501 (2010)). The final model contains the full antibody (two light chains and two heavy chains, two 7-residue sugar chains), 5 sulfate ions and 3 sucrose molecules from the cryoprotectant solution, and 480 water molecules.

Figure 8A:
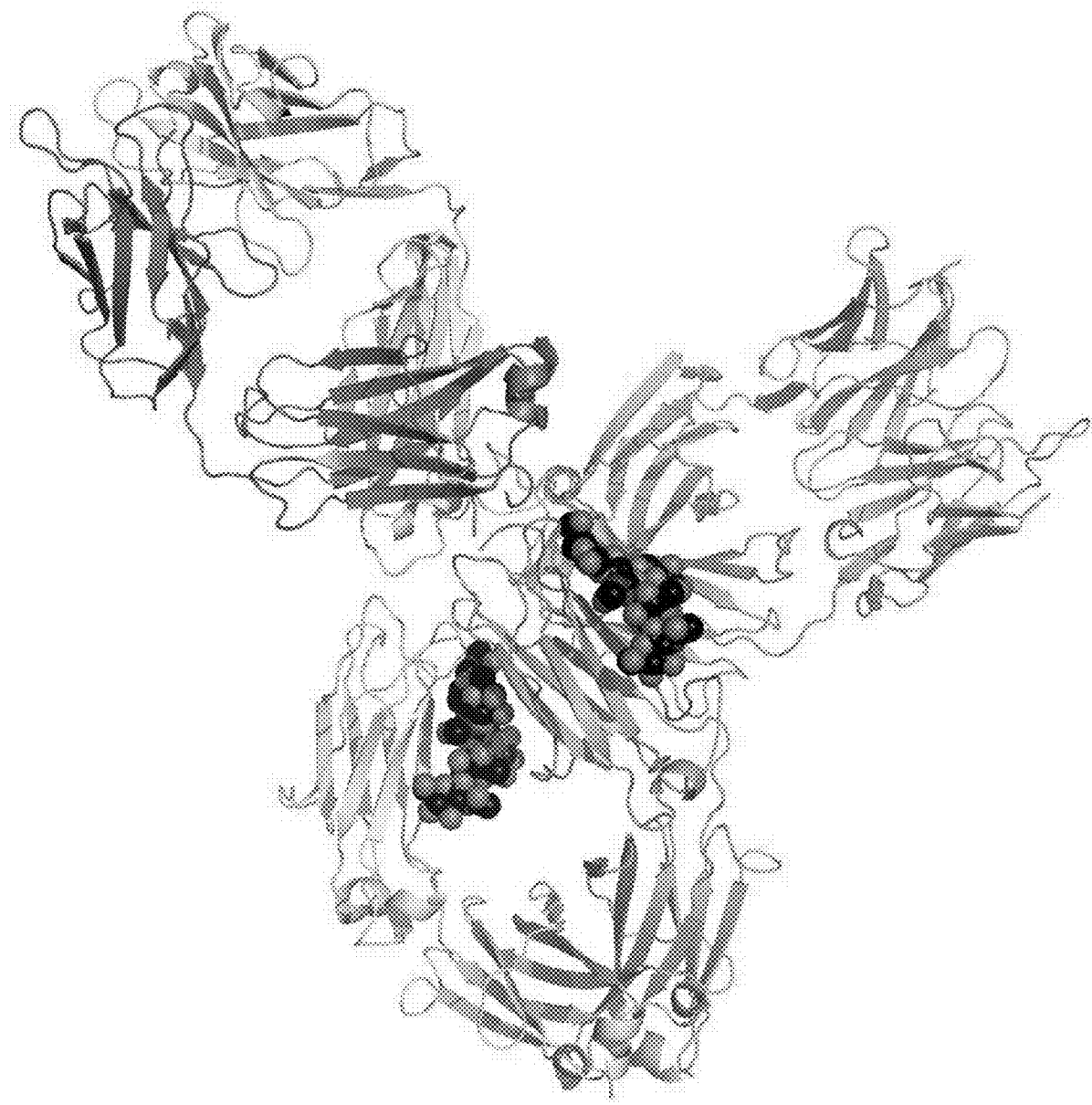
FIGS. 8A and 8B show a ribbon diagram of the pembrolizumab 3-dimensional structure, which was solved by X-ray diffraction analysis of crystals obtained by hanging drop diffusion method at 30° C. using 1.8 M ammonium dihydrogen phosphate, 100 mM Tris-HCl as the precipitant. See Example 7. The ribbon diagram is shown in color in FIG. 8A, with the two heavy chains in yellow and cyan, and the two light chains in magenta (FAB-1) and green (FAB-2), while the same ribbon diagram is shown in grey tones in FIG. 8B.
Figure 8B:
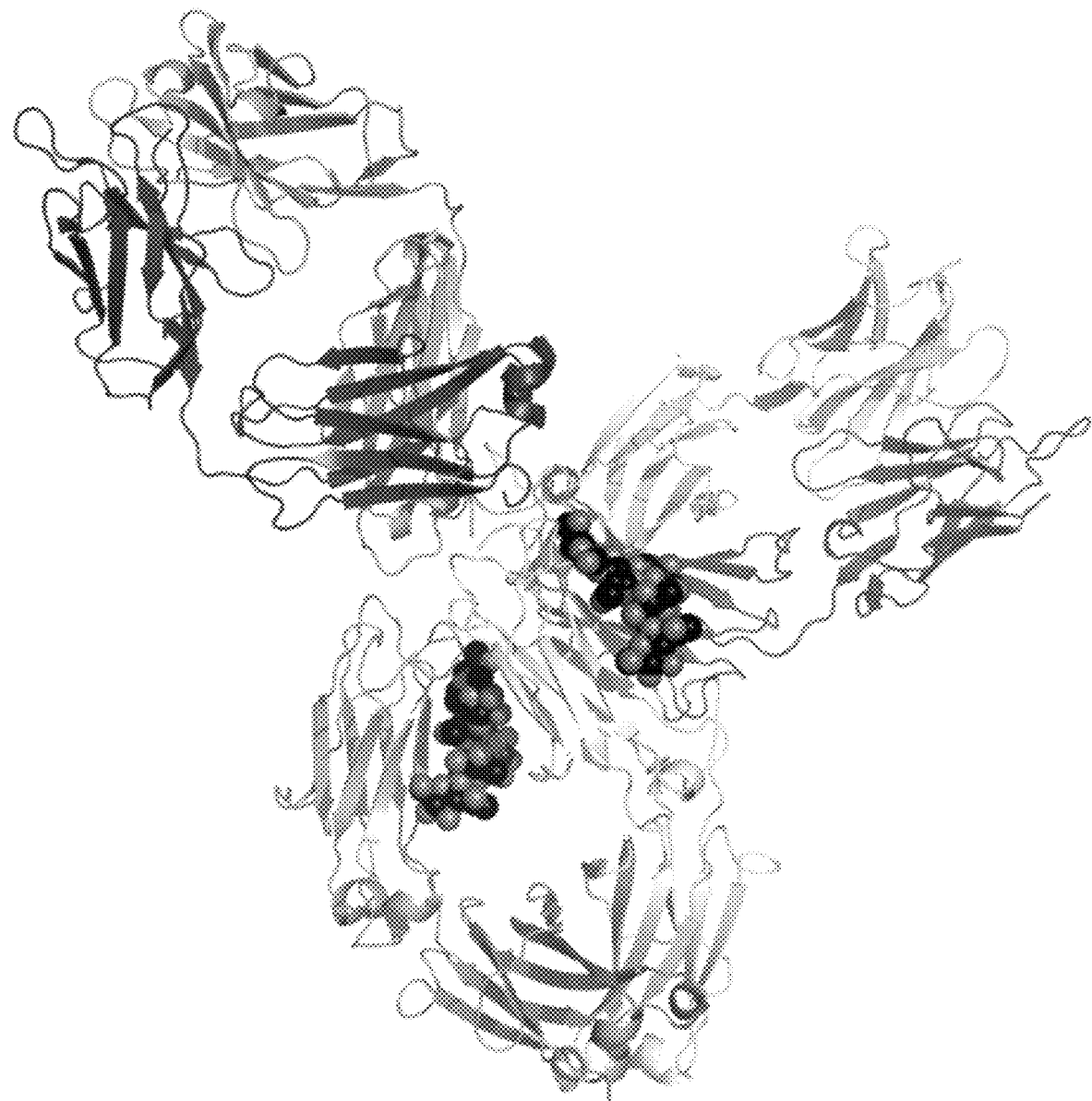

The pembrolizumab structure, which is illustrated in FIG. 8, is a tetramer of about 140 Å wide and 120 Å long. The Fc domain is glycosylated at Asn297 in the CH2 domain on both chains.

Example 8: Vapor Diffusion Crystallization in Ammonium Phosphate Mixtures

Figure 9:
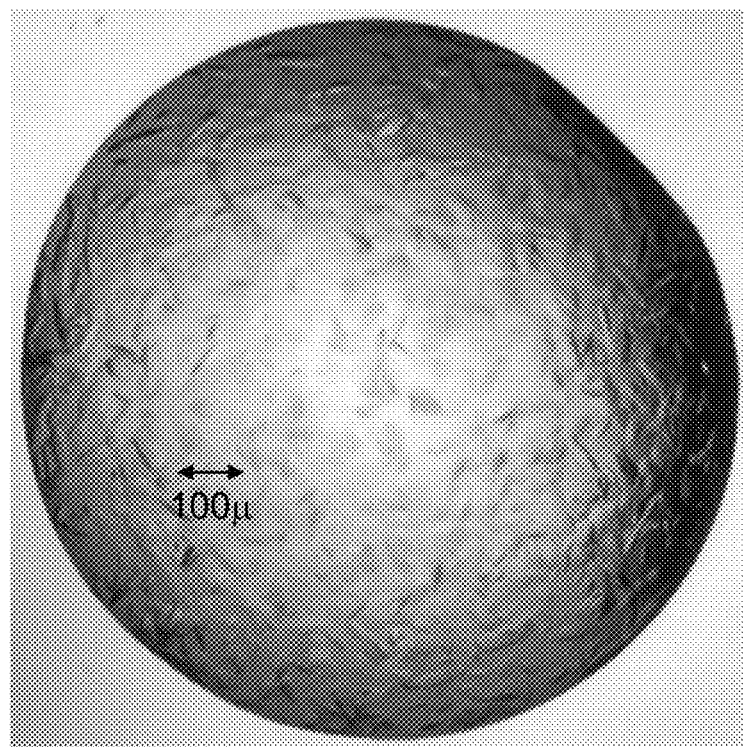
FIG. 9 shows a photomicrograph of crystals within a pembrolizumab crystalline suspension, obtained by vapor diffusion at 30° C. using 1.9 M ammonium dihydrogen phosphate and 0.09 M ammonium hydrogen phosphate as the precipitant. See Example 8. The photomicrograph, at 70× magnification, was taken after 3 days using a Rock Imager system (Formulatrix, Bedford, Mass.), and the double-sided arrow indicates a distance of 20 micron.

This example investigated use of a buffer other than Tris-HCl in the precipitant solution. A pembrolizumab solution (34 mg/ml antibody, 10 mM Histidine, pH 5.6) was screened in sitting drop vapor diffusion experiments using a screening matrix of 96 different ammonium phosphate monobasic/ammonium phosphate dibasic mixtures in which the ratio of the monobasic and dibasic components varied but the total phosphate concentration was kept constant at 1.99 M. Using an Oryx crystallization robot (Douglas Instruments Ltd) a drop consisting of 0.25 ul pembrolizumab solution+0.75 ul of a screen solution was dispensed over 80 ul of the same screen solution in a well of an MRC-2 96 well crystallization plate (Hampton Research). The plate was incubated at 30° C. and monitored using a Rock Imager 1000 system (Formulatrix, Bedford, Mass.). Crystals were observed from 1-56 days. A photomicrograph of crystals observed after 3 days in the 1.9 M ADP, 0.09 M AHP precipitant solution are shown in FIG. 9.

Example 9: Batch Crystallization of Pembrolizumab (1 ml Scale) in Tris/ADP

An antibody mixture is prepared in a 1.5 ml microcentrifuge tube by combining, at 4° C., 167 ul of a pembrolizumab solution (47 mg/ml, 10 mM histidine, pH 5.5) and 833 ul of a precipitant solution (120 mM Tris-HCl, pH 8.4, and 1.9 M ADP). The tube containing the antibody mixture was incubated at 30° C. for 5 days.

Example 10: Batch Dialysis Crystallization of Pembrolizumab in Tris/ADP

Two hundred microliters of a pembrolizumab solution (47 mg/ml antibody, 10 mM Histidine, pH 5.5) is dialyzed in a DispoDialyzer® using a 30 kD molecular weight cutoff membrane (Spectrum Laboratories, Inc., Rancho Dominguez, Calif. USA) against 20 ml of 100 mM Tris-HCl, pH 8.4, 1.9 M ammonium dihydrogen phosphate for 5 days at 30° C. The crystalline suspension is harvested as described in Example 11.

Example 11: Preparation of a Pembrolizumab Solution from a Crystalline Suspension A 210 ul aliquot of crystalline suspension was obtained by combining a number of drops from various vapor diffusion experiments using ADP/Tris-HCl as the precipitant and which contained a total of about 400 mg of pembrolizumab crystals. The aliquot was centrifuged in a Fischer brand microfuge at 5000 rpm for 5 minutes at room temperature. The supernatant (mother liquor) was removed by aspiration and the pellet (pembrolizumab crystals) was re-suspended in 300 ul of stabilizing solution (100 mM Tris-HCl, pH 8.4, 1.9 M ADP). The resulting suspension was centrifuged in a microfuge at 5,000 rpm for 5 minutes at room temperature. The supernatant (wash) was removed by aspiration and the resulting pellet (pembrolizumab crystals) was re-suspended in a 500 ul dissolution buffer (10 mM histidine, pH 5.5) and incubated at 4° C. for 30 minutes. The resulting pembrolizumab solution was clarified by centrifugation in a microfuge at 5,000 rpm for 5 minutes at 4° C. The clarified pembrolizumab solution was used for the characterization studies described in Examples 12 and 13.

Examples 12 and 13. Characterization of Pembrolizumab Solubilized from Pembrolizumab Crystals The following samples were characterized using ELISA and size exclusion chromatography (SEC).

Sample 1: 200 ul of starting pembrolizumab solution (40 mg/ml antibody in 10 mM histidine, pH 5.6);

Sample 2: 500 ul of solubilized pembrolizumab (re-dissolved crystals obtained from the pembrolizumab crystalline suspension as described in Example 11); and Sample 3: 500 ul of 10 mM histidine, pH 5.6 (buffer control)

The biological activity of pembrolizumab in Samples 1 and 2 was measured in a competitive binding ELISA, which measured the ability of pembrolizumab to outcompete PD-L1 and bind to PD-1 receptor molecules immobilized on an ELISA plate. Dose response curves were generated using serial dilutions of the above samples in the presence of a constant concentration of PD-L1. An EC50 value, the concentration of pembrolizumab which exhibits 50% of the maximal binding, was determined for each sample using a four-parameter logistic curve fitting analysis program. Relative potency was calculated by applying Parallel Line Analysis of dose-response curves in SoftMax® Pro 6 software (Molecular Devices, Sunnyvale, Calif.). The competitive binding potency of Sample 2, reported as geometric mean potency relative to Sample 1 with a geometric standard deviation and 95% confidence interval, is shown below.

| Sample Name | GeoMean % RP (n = 4) | % GSD | LCL (95%) | UCL (95%) |
| --- | --- | --- | --- | --- |
| Sample 1 | 100 | 10 | 86 | 115 |
| Sample 2 | 96 | 14 | 78 | 118 |

These results indicate that pembrolizumab that has never been crystallized and pembrolizumab that has been solubilized from pembrolizumab crystals harvested from a crystalline pembrolizumab suspension have comparable biological activity in a competitive binding ELISA.

Figure 10A:
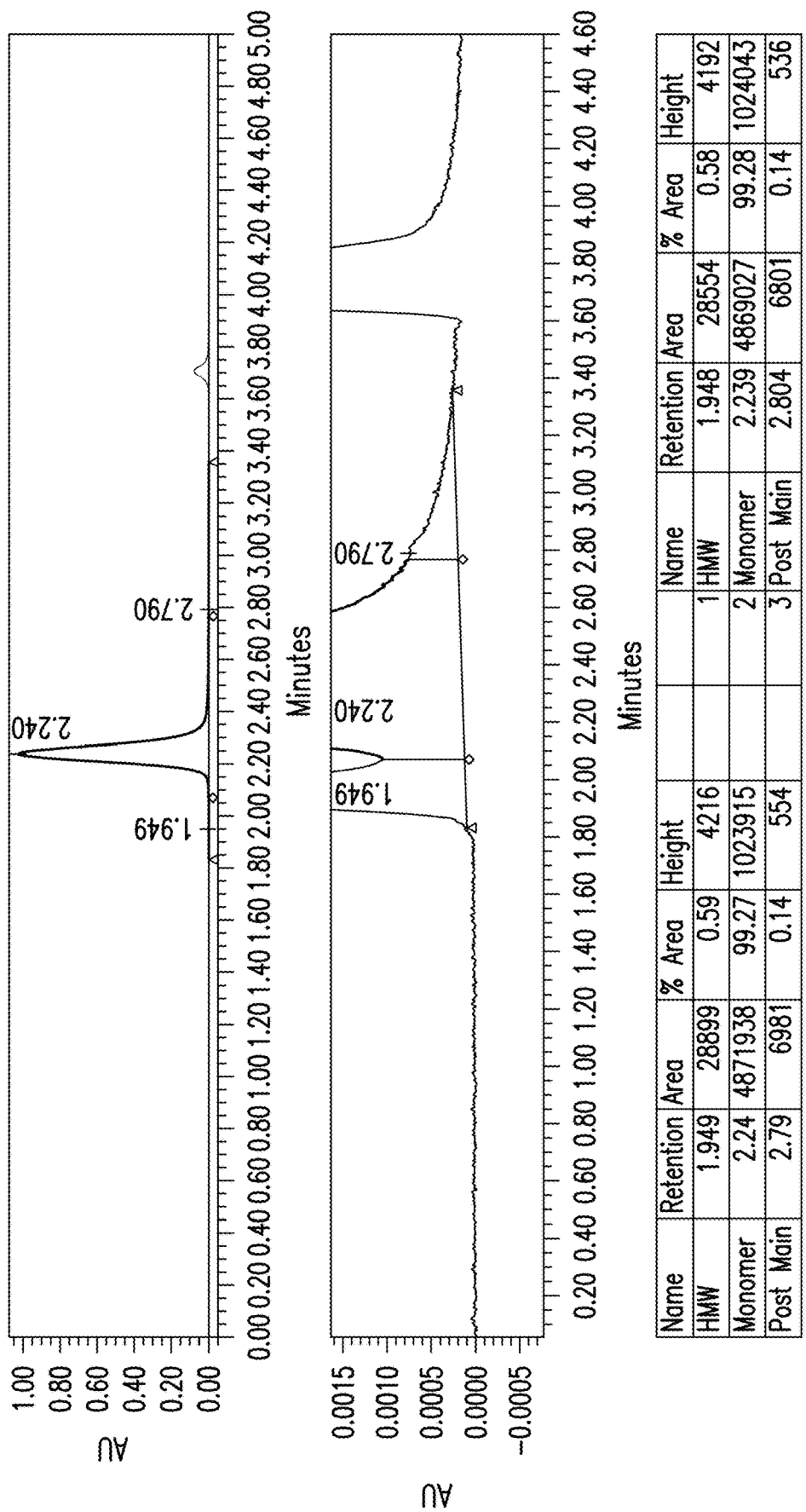
FIGS. 10A and 10B show plots produced by the UPLC-SEC characterization of different pembrolizumab solutions as described in Example 13, showing in FIG. 10A, pembrolizumab that has never been crystallized and in FIG. 10B pembrolizumab solubilized from pembrolizumab crystals.
Figure 10B:
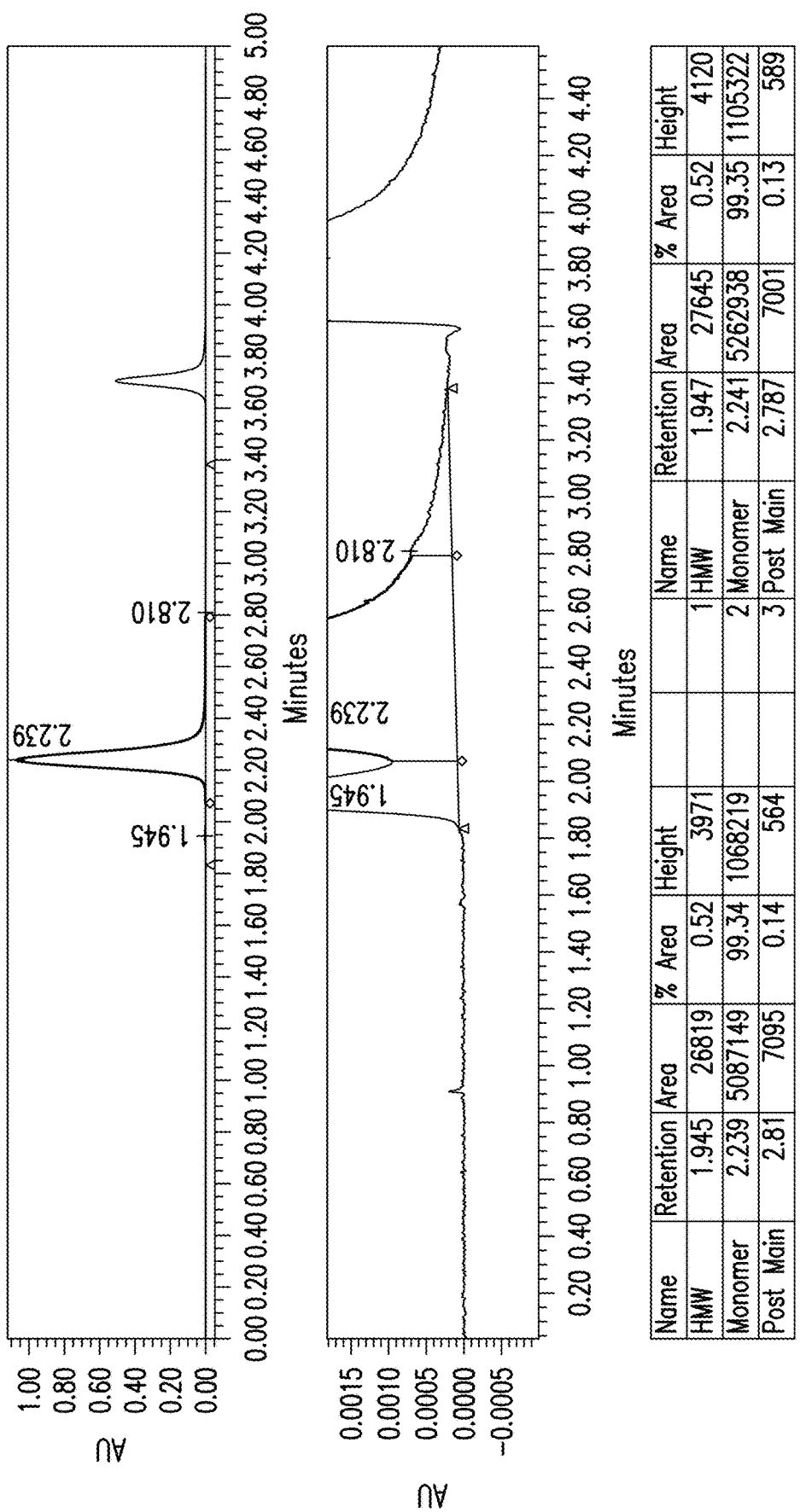

The SEC characterization was performed using an UP-SEC assay, which employed a Waters BEH2000 column (Waters Corp., Milford, Mass., USA; P/N: 186005225) on a Waters Acquity UPLC® system at ambient temperature (25° C.). The sampler was temperature controlled at 4° C. The separation was performed at a flow rate of 0.5 ml/min using 100 mM sodium phosphate, 100 mM NaCl at pH 7.0 as mobile phase. The run time was 5 minutes with A214 as the suggested detection wavelength, and A280 was also collected. Separation plots for each of Samples 1 and 2 are shown in FIGS. 10A and 10B, respectively.

All references cited herein are incorporated by reference to the same extent as if each individual publication, database entry (e.g. Genbank sequences or GeneID entries), patent application, or patent, was specifically and individually indicated to be incorporated by reference. The inclusion of dedicated statements of incorporation by reference, if any, within the specification does not in any way weaken this general statement of incorporation by reference. Citation of a reference herein is not intended as an admission that the reference is pertinent prior art, nor does it constitute any admission as to the contents of or publication date of the reference.

Table 4 provides a brief description of the sequences in the sequence listing.

TABLE 4

| Sequence Identifiers | |
| --- | --- |
| SEQ ID NO: | Description |
| 1 | Pembrolizumab light chain CDR1 |
| 2 | Pembrolizumab light chain CDR2 |
| 3 | Pembrolizumab light chain CDR3 |
| 4 | Pembrolizumab heavy chain CDR1 |
| 5 | Pembrolizumab heavy chain CDR2 |
| 6 | Pembrolizumab heavy chain CDR3 |
| 7 | Pembrolizumab heavy chain |
| 8 | Pembrolizumab light chain |

What is claimed is:

1. A crystal of an anti-PD-1 monoclonal antibody (mAb), wherein the anti-PD-1 mAb is pembrolizumab and the crystal is characterized by unit cell dimensions of a=63.5 to 78.9 Å, b=110.2 to 112.2 Å, c=262.5 to 306 Å, α=90, β=90, γ=90° and a space group of $P2_12_12_1$.

2. The crystal of claim 1, wherein the crystal is characterized by having a length in a range of: 1 to 200 microns.

3. The crystal of claim 1, which is capable of diffracting X-rays to a resolution selected from the group consisting of 2.3 Å to 3.5 Å, 2.3 Å to 3.0 Å, 2.3 Å to 2.75 Å, 2.3 Å to 2.5 Å and 2.3 Å.

4. A method for producing crystals of an anti-PD-1 monoclonal antibody (mAb), wherein the anti-PD-1 mAb is pembrolizumab and the crystal is characterized by unit cell dimensions of a=63.5 to 78.9 Å, b=110.2 to 112.2 Å, c=262.5 to 306 Å, α=90, β=90, γ=90° and a space group of $P2_12_12_1$ and the method comprises exposing a solution comprising the anti-PD-1 mAb to a precipitant solution at a temperature that is at least 25° C. and is no greater than 50° C. for a time sufficient for crystal formation, wherein the precipitant solution has a pH of 4.0 to 5.0 and comprises 1.0 M to 2.5 M ammonium dihydrogen phosphate.

5. The method of claim 4, wherein the exposing step comprises mixing the antibody solution and the precipitant solution to form a crystallization mixture and applying a crystallization process to the mixture, wherein the crystallization process is selected from the group consisting of hanging drop vapor diffusion, sitting drop vapor diffusion and batch.

6. The method of claim 5, wherein the crystallization process is a batch process and the method further comprises seeding the crystallization mixture with crystals of the anti-PD-1 mAb.

7. The method of claim 4, wherein the antibody solution comprises the anti-PD-1 mAb at a concentration of 2 to 200 mg/ml, 3 to 100 mg/ml, 10 to 90 mg/ml, 20 to 80 mg/ml, 30 to 70 mg/ml, 40 to 60 mg/ml or about 50 mg/ml and the precipitant solution has a pH selected from the group consisting of 4.2 to 4.8, 4.4 to 4.6 and 4.5.

8. The method of claim 7 wherein the precipitant solution comprises (a) 1.5 M to 2.0 M ammonium dihydrogen phosphate and 100 to 120 mM Tris-HCl or (b) 1.9 M ammonium dihydrogen phosphate and 0.09 M ammonium hydrogen phosphate.

9. The method of claim 8, wherein the exposing step is performed for at least 3, 4 or 5 days at a temperature of about 30° C.

10. A method for crystallizing an anti-PD-1 monoclonal antibody (mAb) from a solution comprising the anti-PD-1 mAb, wherein the antibody is pembrolizumab and the method comprises: (a) combining the anti-PD-1 mAb solution with a precipitant solution and seed crystals of the anti-PD-1 mAb to produce a seeded crystallization mixture; (b) incubating the seeded crystallization mixture at a temperature of at least 20° C. and no greater than about 40° C.; and (c) harvesting the crystals, wherein the seed crystals are from a seed stock of crystals of the anti-PD-1 mAb that were produced by a method of claim 4.

11. A pharmaceutical composition comprising (a) crystals of an anti-PD-1 monoclonal antibody (mAb), wherein the antibody is pembrolizumab and the crystal is characterized by unit cell dimensions of a=63.5 to 78.9 Å, b=110.2 to 112.2 Å, c=262.5 to 306 Å, α=90, β=90, γ=90° and a space group of $P2_12_12_1$ and (b) at least one pharmaceutically acceptable excipient.

12. The composition of claim 11, herein the anti-PD-1 mAb crystals are suspended in a liquid and the anti-PD-1 mAb concentration in the composition is at least 50 mg/ml, at least 100 mg/ml, at least 200 mg/ml or at least 250 mg/ml.

13. The composition of claim 11, which is a solid.

14. A method of treating a human subject for a cancer, which comprises administering to the patient a therapeutically effective amount of a pharmaceutical composition of claim 11.

15. The method of claim 14, wherein the cancer is bladder cancer, breast cancer, clear cell kidney cancer, head/neck squamous cell carcinoma, lung squamous cell carcinoma, malignant melanoma, non-small-cell lung cancer (NSCLC), ovarian cancer, pancreatic cancer, prostate cancer, renal cell cancer, small-cell lung cancer (SCLC), triple negative breast cancer, acute lymphoblastic leukemia (ALL), acute myeloid leukemia (AML), chronic lymphocytic leukemia (CLL), chronic myeloid leukemia (CIVIL), diffuse large B-cell lymphoma (DLBCL), EBV-positive DLBCL, primary mediastinal large B-cell lymphoma, T-cell/histiocyte-rich large B-cell lymphoma, follicular lymphoma, Hodgkin's lymphoma (HL), mantle cell lymphoma (MCL), multiple myeloma (MM), myeloid cell leukemia-1 protein (Mcl-1), myelodysplastic syndrome (MDS), non-Hodgkin's lymphoma (NHL), or small lymphocytic lymphoma (SLL).

16. The method of claim 15, wherein the pharmaceutical composition comprises at least 200 mg/ml of the mAb and is administered subcutaneously.

17. The method of claim 15, wherein the cancer is a solid tumor and a tissue section of the cancer removed from the subject prior to a first administration of the pharmaceutical composition tested positive for expression of one or both of PD-L1 and PD-L2.

18. A method for producing crystals of an anti-PD-1 monoclonal antibody (mAb), wherein the anti-PD1 mAb is pembrolizumab and the method comprises exposing a solution comprising the anti-PD-1 mAb to a precipitant solution at a temperature that is at least 25° C. and is no greater than 50° C. for a time sufficient for crystal formation, wherein the precipitant solution has a pH of 4.0 to 5.0 and comprises 1.0 M to 2.5 M ammonium dihydrogen phosphate.

\* \* \* \* \*